United States Patent [19]

Moser et al.

[11] Patent Number: 5,078,780
[45] Date of Patent: Jan. 7, 1992

[54] 1,5-DIPHENYLPYRAZOLE-3-CARBOXYLIC ACID DERIVATIVES FOR THE PROTECTION OF CULTIVATED PLANTS

[75] Inventors: Hans Moser, Magden; Beat Böhner, Binningen; Werner Föry, Riehen, all of Switzerland

[73] Assignee: Ciba-Geigy Corporation, Ardsley, N.Y.

[21] Appl. No.: 109,667

[22] Filed: Oct. 16, 1987

[30] Foreign Application Priority Data

Oct. 22, 1986 [CH] Switzerland ............ 4215/86
Oct. 22, 1986 [CH] Switzerland ............ 4217/86

[51] Int. Cl.$^5$ ............ A01N 43/56; A01N 43/60; A01N 43/76; A01N 43/78
[52] U.S. Cl. ............ 71/92; 47/57.6; 71/90; 544/82; 544/140; 546/187; 546/211; 546/279; 548/378
[58] Field of Search ............ 548/378; 71/90, 92; 544/82, 140; 546/187, 211, 279; 47/57.6

[56] References Cited

U.S. PATENT DOCUMENTS 4,116,673  7/1978  Branningan ............ 71/92

Primary Examiner—Robert W. Ramsuer
Attorney, Agent, or Firm—Edward McC. Roberts

[57] ABSTRACT 1,5-diphenylpyrazole-3-carboxylic acid derivatives of the formula

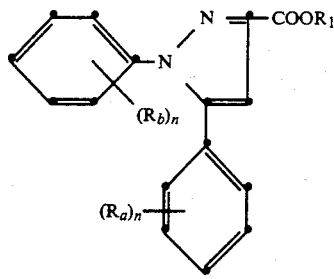

are capable of antagonising specifically the phytotoxic action of phenoxypropionic acid ester herbicides of the formula II

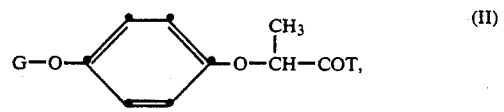

in which G represents

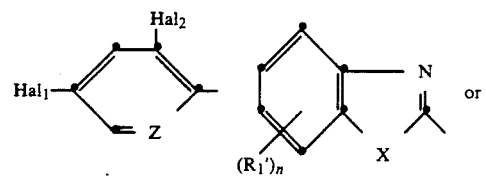

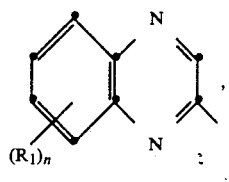

Compositions, containing those compositions, as selective herbicides and the use of those two active ingredients for controlling weeds in crops of useful plants are described, as are also novel 1,5-diphenylpyrazole-3-carboxylic acid derivatives corresponding to the formula I and the preparation thereof.

10 Claims, No Drawings

1,5-DIPHENYLPYRAZOLE-3-CARBOXYLIC ACID DERIVATIVES FOR THE PROTECTION OF CULTIVATED PLANTS

The present invention relates to novel 1,5-diphenylpyrazole-3-carboxylic acid derivatives and to the use thereof for the protection of cultivated plants against the harmful effect of herbicidally active phenoxyalkanecarboxylic acid esters, and to herbicidal compositions containing these 1,5-diphenylpyrazole-3-carboxylic acid derivatives or a combination of a herbicide and a 1,5-diphenyl-3-pyrazolecarboxylic acid derivative as antagonist. The invention relates also to the novel 1,5-diphenylpyrazole-3-carboxylic acid derivatives and to the preparation thereof.

When using phenoxyalkanecarboxylic acid herbicides, such as, for example, phenoxyphenoxy- and pyridyloxyphenoxy-propionic acid derivatives, the cultivated plants can be considerably damaged, depending on factors, such as, for example, the amount of herbicide and the method of application, the type of cultivated plant, soil condition and climatic conditions, such as, for example, hours of daylight, temperature and amounts of rainfall. Severe damage may occur especially when, within the framework of the crop rotation, cultivated plants that are resistant to the herbicides are to be followed by other cultivated plants that have no, or only insufficient, resistance to the herbicides.

It has surprisingly now been found that it is possible to protect cultivated plants against damage caused by herbicidally active phenoxypriopionic acid derivatives by treating the cultivated plants, parts of those plants or land intended for growing the cultivated plants with a safener selected from a group of 1,5-diphenylpyrazole-3-carboxylic acid derivatives. The herbicidal action against weeds and weed grasses is not cancelled by those derivatives.

1,5-diphenylpyrazole-3-carboxylic acid derivatives that are suitable for the protection of cultivated plants from the harmful effects of herbicidally active phenoxyphenyoxy-, pyridin-2-yloxyphenoxyl-, benzoxazolyloxyphenoxy-, benzothiazolyloxyphenoxy- or quinoxalinyloxyphenoxy-propionic acid derivatives, correspond to the formula I

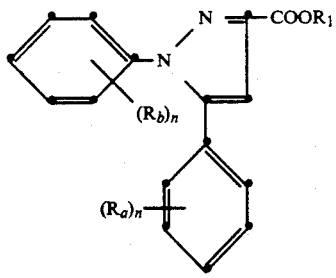

in which each of $R_1$ and $R_b$, independently of the other, represents halogen, $C_1$–$C_5$-alkyl, $C_1$–$C_5$-haloalkyl, $C_2$–$C_5$-alkenyl, $C_2$–$C_5$-alkynyl or cyano, n represents zero or an integer from 1 to 3 and the group —$OR_1$ represents hydroxy, a salt radical or any desired ester radical.

In the radical —$OR_1$: $R_1$ represents especially hydrogen, a plant-physiologically tolerable metal or ammonium cation, a $C_1$–$C_{18}$-alkyl or $C_3$–$C_{18}$-cycloalkyl radical that is unsubstituted or mono- or polysubstituted by $C_2$–$C_8$-alkenyl, $C_2$–$C_8$alkynyl, $C_3$–$C_8$-cycloalkenyl, n cyan or by an —$XR_{10}$, —$CXR_{10}$, —$CX$—$XR_{10}$, —$CXNR_3R_4$, —$XCXR_{10}$, —$XCXNR_3R_4$, —$NR_3R_4$, —$NR_3CONR_3R_4$, —$CONR_3$ —$NR_3R_4$, —$CONR_3$—$NR_3COR_4$, —$Si(C_1$–$C_4alkyl)_3$, —$C(OR_7)(OR_8)OR_9$ or $PO(R_5)R_6$ radical; a heterocycle Q that is bonded via C or N; an unsubstituted or substituted phenyl or naphthyl radical U, a radical E–U or an imido radical —$N$=$C(R_2)R_2$, $R_2$ represents especially $C_1$–$C_4$-alkyl or $C_3$–$C_7$-cycloalkyl, or the two radicals $R_2$ together represent especially a 4- to 6-membered $C_4$–$C_{12}$-alkylene radical that may be branched and/or interrupted by oxygen or sulphur, each of $R_3$ and $R_4$, independently of the other, represents especially hydrogen, or $C_1$–$C_8$-alkyl or $C_3$–$C_8$-cycloalkyl each of which is unsubstituted or substituted by $C_2$–$C_6$-alkenyl, $C_2$–$C_6$-alkynyl, $C_3$–$C_7$-cycloalkyl, halogen, $C_1$–$C_8$-alkoxy, $C_2$–$C_8$-alkoxyalkoxy, $C_1$–$C_8$-alkythio or by cyano, and one of $R_3$ and $R_4$ alternatively represents $C_1$–$C_8$-alkoxy, —$COOR_{10}$, —$CONH_2$, $CONH(C_1$–$C_4$-alkyl), $CON(R_2)R_2$, —$NH_2$, —$NH$ ($C_1$–$C_2$alkyl)—$N(R_2)R_2$, a heterocycle Q, or a phenyl or naphthyl radical U that is bonded to the nitrogen atom directly or via a $C_1$–$C_{14}$-alkylene bridge, $R_3$ and $R_4$ together represent especially a 4- to 6-membered $C_4$–$C_{12}$-alkylene or -alkenylene chain that may branched and/or interrupted by oxygen, sulphur, N ($C_4$–$C_4$-alkyl), N(benzyl), —$SO_2$—, —$CO$— or by —$C(OR_7)OR_8$, and that may be substituted by halogen, $C_1$–$C_4$-alkyl, $C_1$–$C_4$-alkoxy, —$NH_2$, —$NH$ ($C_1$–$C_4$-alkyl) or by —$N(C_1$–$C_4$-alkyl)$_2$, each of $R_5$ and $R_6$, independently of the other, represents especiall $C_1$–$C_4$-alkyl, hydroxy or $C_1$–$C_4$-alkoxy, each of $R_7$ and $R_8$, independently of the other, represents especially $C_1$–$C_4$-alkyl, $R_7$ and $R_8$ together represent especially $C_2$–$C_4$-alkylene, each of $R_9$ and $R_{10}$, independently of the other, represents especially hydrogen, or $C_1$–$C_8$-alkyl or $C_3$–$C_8$-cycloalkyl each of which is unsubstituted or substituted by $C_2$–$C_6$-alkenyl, $C_2$–$C_6$-alkynyl, $C_3$–$C_6$-cycloalkenyl, halogen, $C_1$–$C_4$-alkoxy, $C_2$–$C_8$-alkoxyalkoxy, $C_1$–$C_6$-alkoxycarbonyl, $C_1$–$C_6$-haloalkoxycarbonyl, a heterocycle Q or by a phenyl or naphthyl radical U, $R_9$ and $R_{10}$ also represent especially the phenyl or naphthyl radical U, or a heterocycle Q bonded via C, Q represents especially a saturated or unsaturated 5- to 12-membered heterocycle that contains from 1 to 4 hetero atoms N, O or S or a —SO—, —$SO_2$—, $N(C_1$–$C_4$-allyl) or N(benzyl) group and that may be substituted by halogen, $C_1$–$C_4$-alkyl, $C_1$–$C_4$-alkoxy, $C_1$–$C_4$-haloalkyl, $C_1$–$C_4$-haloalkoxy, cyano or by nitro, E represents especially a $C_1$–$C_4$-alkylene bridge, a $C_3$–$C_4$-alkenylene bridge or a $C_3$–$C_4$-alkynylene bridge, U represents especially a phenyl or naphthyl radical that is unsubstituted or mono- or poly-substituted by halogen, $C_1$–$C_4$-alkyl, $C_1$–$C_4$-alkyl, $C_1$–$C_4$-alkylsulphinyl, $C_1$–$C_4$-alkylsulphonyl, $C_1$–$C_4$-haloalkyl, $C_1$–$C_4$-haloalkoxy, cyano, nitro, —COOH, —$COOC_1$–$C_4$-alkyl, —$COC_1$–$C_4$-alkyl, $CONH_2$, $CONH(C_1$–$C_4$-alkyl), $CON(C_1$–$C_4$-alkyl)$_2$, —$SO_2NH_2$, $SO_2NH(C_1$–$C_4$-alkyl), $SO_2N(C_1$–$C_4$-alkyl), pyrrolidino, piperidino or by the pyrrolidinocarbonyl, piperidinocarbonyl or morpholinocarbonyl radical, and X represents especially oxygen or sulphur.

Plant-physiologically tolerable metal and ammonium cations should be understood as meaning the cations of salts customarily used in herbicides, such as alkali metal, alkaline earth metal, iron, copper, manganese or ammonium-alkylammonium, hydroxyalkylammonium or alkoxyalkylammonium cations.

Alkyl radicals should be understood as meaning radicals having the specified number of carbon atoms. These radicals may be straight-chained or branched. The most usual radicals are, for example, methyl, ethyl, n-propyl, isopropyl, n-butyl, isobutyl, sec.-butyl, tert.-butyl, n-pentyl, isopentyl, n-hexyl and n-octyl. The alkenyl and alkynyl radicals may also be straight-chained or branched and they contain from 3 to 6 carbon atoms. The most common radicals are, for example, allyl, methallyl, butene, butadiene, propynyl, methylpropynyl, 1-butynyl and 2-butynyl. Cycloalkyl or cycloalkenyl radicals have preferably from 3 to 12 carbon atoms and may also be benzo-fused. Typical representatives are, for example, cyclopropyl, cyclopentyl, cyclohexyl, cyclohexenyl, indan, tetrahydronaphthalene and Decalin. Halogen should be understood as meaning fluorine, chlorine, bromine or iodine, especially fluorine or chlorine. Haloalkyl and haloalkenyl radicals may be mono- or poly-substituted by halogen.

The radical Q is a saturated or unsaturated 5- to 12-membered heterocycle which may also contain one, two or three further hetero atoms or a sulphinyl or sulphonyl group, may be interrupted by one or two carbonyl groups and which may be benzo-fused, unsubstituted or substituted.

Suitable hetero atoms are one, two or three further nitrogen atoms and up to two sulphur or oxygen atoms, although 2 oxygen atoms may not be directly vicinal.

Examples of such heterocycles are given below: pyrroline, pyrrolidine, imidazoline, imidazolidine, pyrazoline, pyrazolidine, isoxazoline, isoxazolidine, oxazoline, oxazolidine, isothiazolidine, thiazolines, thiazolidines, dithiazolidines, oxadiazolidines, pyridine, piperidine, piperazine, tetrahydro-pyrimidine and -pyrazine, pyrimidine, pyridazine, morpholine, thiomorpholine, thiazines, hexahydrotriazines, tetrahydrotriazines, oxadiazines, oxatriazines, hexahydroazepine, hexahydrodiazepines, diazepines, hexahydrooxazepines, azacyclooctane, benzofuran, benzothiophene, indole, indoline, isoindoline, benzimidazoline, benzindazoline, benzoxazoline, benzothiazolines, benzisoxazoline, benzotriazole, quinoline, tetrahydroquinoline, tetrahydroisoquinoline, quinazoline, quinoxaline, phthalazine, benzomorpholine, benzothiomorpholine, tetrahydrobenz-azepines and -diazepines, tetrahydrobenzoxazepines, 1,5-diazabicyclo[4.3.0]nonanes, dihydrobenzoxazines, 1,6-diazabicyclo[5.3.0]decanes, 1,4-diazabicyclo[3.3.0]-octanes and 1,5-diazabicyclo[4.4.0]decanes.

The above-mentioned heterocycles may also be substituents. Further examples of heterocyclic systems having a substituent function are, for example, pyrrole, imidazole, pyrazole, isoxazole, oxazole, isothiazole, thiazole, triazoles, oxadiazoles, thiadiazoles, tetrazoles, oxatriazoles, thiatriazoles, furan, tetrahydrofuran, dioxoles, dioxolanes, oxathiols, oxathiolanes, thiophene, tetrahydrothiophene, dithiolanes, dithiazoles, pyridine, pyrans, thiopyrans, pyridazine, pyrimidine, pyrazine, tetrahydropyran, tetrahydrothiopyran, dioxines, dioxans, dithiins, dithianes, oxazines, thiazines, oxathiins, oxathianes, triazines, oxadiazines, thiadiazines, oxathiazines, dioxazines, azepines, oxepins, thiepines, diazepines, oxazepins, indoles, benzofurans, benzothiophenes, indazoles, benzimidazoles, benzodioxoles, benzodithiols, benzisoxazoles, benzothiazoles, benzoxazoles, benzoxathiols, benzotriazoles, benzoxadiazoles, benzofurazan, benzothiadiazoles, quinoline, isoquinoline, chromenes, chroman, isochromene, isochroman, thiochromenes, isothiochromenes, thiochroman, isothiochroman, cinnoline, quinazoline, quinoxaline, phthalazine, benzodioxines, benzodithiins, benzoxazines, benzodioxans, benzoxathianes, benzotriazines, benzazepines, benzodiazepines, benzoxazepines, purines, pteridines, phenoxazines and phenothiazines.

The heterocyclic radicals may be substituted by halogen $C_1$-$C_4$-alkyl, $C_1$-$C_4$-alkoxy, $C_1$-$C_4$-haloalkyl, $C_1$-$C_4$-haloalkoxy, cyano or by nitro.

The pyrazole derivatives of the formula I have an outstanding ability to protect cultivated plants against the harmful effect of herbicidally active 2-[4-(phenoxy, pyridin-2-yloxy, benzoxazolyloxy, benzothiazolyloxy and quinoxalin-2-yloxy)-phenoxy]-propionic acid esters of the formula II

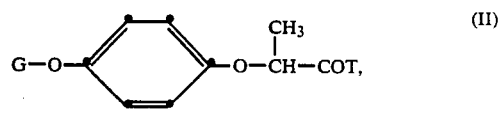

in which G represents

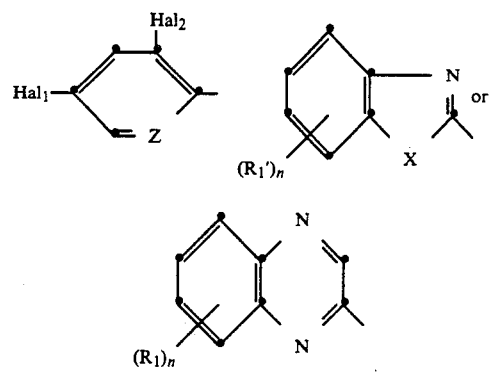

in which $Hal_1$ represents fluorine, chlorine, bromine, iodine or trifluoromethyl, $Hal_2$ represents hydrogen, fluorine, chlorine, bromine or trifluoromethyl, Z represents nitrogen or methine —CH=, X represents an oxygen or sulphur atom, $R_1$ represents halogen, trifluoromethyl, nitro, cyano, $C_1$-$C_4$-alkyl or $C_1$-$C_4$-alkoxy and n represents 0, 1, 2 or 3.

In the compounds of the formula II, halogen represents fluorine, chlorine, bromine or iodine, preferably fluorine, chlorine or bromine.

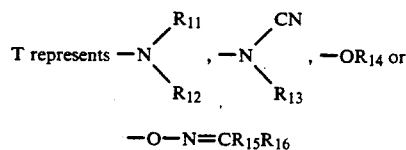

$$-O-N=CR_{15}R_{16}$$

in which each of $R_{11}$ and $R_{12}$, independently of the other, represents hydrogen, $C_1$-$C_8$-alkoxy, $C_1$-$C_8$-alkyl, phenyl or benzyl, and $R_{11}$ and $R_{12}$ together with the nitrogen atom carrying them represent a 5- or 6-membered saturated nitrogen heterocycle that may be interrupted by an oxygen or sulphur atom, $R_{13}$ represents $C_1$-$C_4$-alkyl, $C_3$-$C_4$-alkenyl, $C_3$-$C_4$-alkynyl or $C_2$-$C_4$-alkoxyalkyl, $R_{14}$ represents hydrogen or the equivalent of an alkali metal ion, an alkaline earth metal ion, a copper ion or an iron ion; a quaternary $C_1$-$C_4$-alkylammonium or $C_1$–$C_4$-hydroxyalkylammonium radical; a $C_1$–$C_9$-alkyl radical that is unsubstituted or mono- or polysubstituted by amino, halogen, hydroxy, cyano, nitro, phenyl $C_1$–$C_4$-alkoxy, polyethoxy having from 2 to 6 ethylene oxide units, —COOR, —COSR, —CONH$_2$—, —CON($C_1$–$C_4$-alkoxy)-$C_1$–$C_4$-alkyl, —CO—N-di-$C_1$–$C_4$-alkyl, —CONH-$C_1$–$C_4$- alkyl, —N($C_1$–$C_4$-alkoxy)-$C_1$–$C_4$-alkyl or by di-$C_1$–$C_4$-alkylamino; a $C_3$–$C_9$-alkenyl radical that is unsubstituted or substituted by halogen or by $C_1$–$C_4$-alkoxy; or a $C_3$–$C_9$-alkynyl radical that is unsubstituted or substituted by halogen or by $C_1$–$C_4$-alkoxy; $C_3$–$C_9$-cycloalkyl; or phenyl that is unsubstituted or substituted by cyano, $C_1$–$C_4$-alkyl, $C_1$–$C_4$-alkoxy, acetyl, —COOR$_{17}$, —COSR$_{17}$, —CONH$_2$, —CON($C_1$–$C_4$-alkoxy)-$C_1$–$C_4$-alkyl, —CO—N-di-$C_1$–$C_4$-alkyl or by —COHN—$C_1$–$C_4$-alkyl, each of $R_{15}$ and $R_{16}$, independently of the other, represents $C_1$–$C_4$-alkyl or they together represent a 3- to 6-membered alkylene chain and $R_{17}$ represents hydrogen, $C_1$–$C_6$-alkyl, $C_1$–$C_6$-haloalkyl, $C_2$–$C_6$-alkoxyalkyl, $C_3$–$C_6$-alkenyl, $C_3$–$C_6$-haloalkenyl, $C_3$–$C_6$-alkynyl or $C_3$–$C_6$-haloalkynyl.

In the compounds of the formula II, halogen, as an independent substituent or as part of another substituent, such as haloalkyl, haloalkoxy, haloalkenyl or haloalkynyl, is fluorine, chlorine, bromine or iodine, among which fluorine and chlorine are preferred.

Depending on the number of carbon atoms present, alkyl is methyl, ethyl, n-propyl, i-propyl or isomeric butyl, pentyl, hexyl, heptyl or octyl. The alkyl groups contained in the radicals alkoxy, alkoxyalkyl, haloalkyl and haloalkoxy are identical. Alkyl groups having a low number of carbon atoms are preferred in each case.

Preferred haloalkyl radicals, or haloalkyl moieties in haloalkoxy radicals, are: fluoromethyl, difluoromethyl, trifluoromethyl, chloromethyl, trichloromethyl, 2-fluoroethyl, 2,2,2-trifluoroethyl, 1,1,2,2-tetrafluoroethyl, perfluoroethyl, 2-chloroethyl, 2,2,2-trichloroethyl, 2-bromoethyl and 1,1,2,3,3,3-hexafluoropropyl.

Cycloalkyl is a mono- or bi-cyclic saturated hydrocarbon ring system, such as cyclopropyl, cyclobutyl, cyclopentyl, cyclohexyl, cycloheptyl, cyclooctyl, cyclononyl, bicyclo[4.3.0]nonyl, bicyclo[5.2.0]nonyl or bicyclo[2.2.2]octyl.

Especially noteworthy is the protective action of pyrazole derivatives of the formula I against herbicides of the formula II in which T represents the group —O—$R_{14}$ or —O—N=$CR_{15}R_{16}$ in which $R_{14}$ represents hydrogen, $C_1$–$C_4$-alkyl or $C_3$–$C_4$-alkynyl, or $C_1$–$C_4$-alkyl that is substituted by $C_1$–$C_4$-alkoxycarbonyl or by di-$C_1$–$C_4$-alkylamino, and each of $R_{15}$ and $R_{16}$, independently of the other, represents $C_1$–$C_4$-alkyl or $R_{15}$ and $R_{16}$ together represent a $C_4$–$C_7$-alkylene chain.

Individual meanings of T that should be given special mention are methoxy, ethoxy, propoxy, isopropoxy, butoxy, dimethylaminoethoxy, propargyloxy, 1-cyano-1-methylethoxy, methoxycarbonylmethylthio, 1-ethoxy-carbonylethoxy, butoxycarbonyl, —O—N=C(CH$_3$)$_2$, —O—N=C(CH$_3$)C$_2$H$_5$ or —O—N=C(CH$_2$)$_5$, and of G:

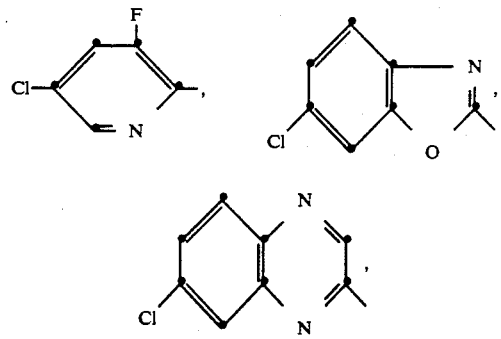

especially
2-[4-(6-chlorobenzoxazol-2-yloxy)-phenyoxy]-propionic acid ethyl ester,
2-[4-(6-chloroquinoxalin-3-yloxy)-phenyoxy]-propionic acid ethyl ester, and the
2-[4-(5-chloro-3-fluoropyridin-2-yloxy)-phenyoxy]-propionic acid derivatives in Table 1.

TABLE 1

(II)

$$Cl\text{–}\underset{N}{\diagdown}\text{–}\diagup\text{–}O\text{–}\diagdown\diagup\text{–}O\text{–}\underset{CH_3}{\overset{|}{CH}}\text{–}CO\text{–}Y$$

| No. | Y | physical constant |
|---|---|---|
| 2.1 | —OCH$_3$ | m.p. 63–64° C. |
| 2.2 | —OC$_4$H$_9$-n | $n_D^{35}$ = 1.5275 |
| 2.3 | —O—N=C(CH$_3$)$_2$ | $n_D^{35}$ = 1.5488 |
| 2.4 | —OC$_2$H$_5$ | $n_D^{35}$ = 1.5358 |
| 2.5 | —O—CH$_2$—CH$_2$—N(CH$_3$)$_2$ | $n_D^{35}$ = 1.5334 |
| 2.6 | —O—CH$_2$—C≡CH | $n_D^{35}$ = 1.5492 |
| 2.7 | —O—C(CH$_3$)(CH$_3$)—CN | $n_D^{35}$ = 1.5330 |
| 2.8 | —S—CH$_2$—COOCH$_3$ | $n_D^{35}$ = 1.5607 |
| 2.9 | —O—CH(CH$_3$)—COOC$_2$H$_5$ | $n_D^{35}$ = 1.5227 |
| 2.10 | —O—CH$_2$—COOC$_4$H$_9$-n | $n_D^{35}$ = 1.5223 |
| 2.11 | —OC$_3$H$_7$-n | $n_D^{35}$ = 1.5319 |
| 2.12 | —OC$_3$H$_7$-i | $n_D^{35}$ = 1.5284 |
| 2.13 | —O—N=C(CH$_3$)—C$_2$H$_5$ | $n_D^{35}$ = 1.5340 |
| 2.14 | —O—N=C (cyclopentyl) | $n_D^{35}$ = 1.5360 |
| 2.15 | —OCH$_3$ (2R) | $n_D^{35}$ = 1.5359 |
| 2.16 | —OH | m.p. 95–97° C. |
| 2.17 | —S—CH$_2$—COOCH$_3$ (2R) | $n_D^{35}$ = 1.5623 |
| 2.18 | —O—CH(CH$_3$)—COOC$_2$H$_5$ (2R,S) | $n_D^{35}$ = 1.5223 |
| 2.19 | —O—CH$_2$—C≡CH (2R) | m.p. 55–56° C. |
| 2.20 | —NH—OCH$_3$ | m.p. 103–105° C. |

Very special mention should be made of compound 2.19

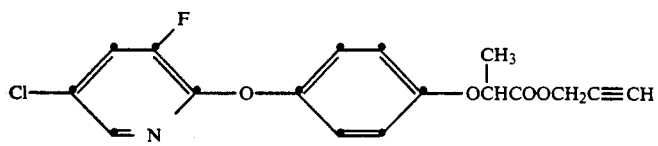

and its 2R enantiomer.

The optically active carbon atom of the propionic acid group can be present in the R- as well as in the S-configuration. Unless otherwise indicated, it should be understood that the racemic mixtures are included in each case. Preferred herbicides of the formula II have the 2R configuration.

As cultivated plants that can be protected by 1,5-diphenylpyrazole-3-carboxylic acid derivatives of the formula I against the harmful effects of herbicides of the formula II there come into consideration especially those which are important in the food or textile sector, for example sugar cane and especially sorghum, corn, rice and other types of cereal (wheat, rye, barley, oats).

The invention relates also to the novel 1,5-di-phenyl-pyrazole-3-carboxylic acid derivatives of the formula I

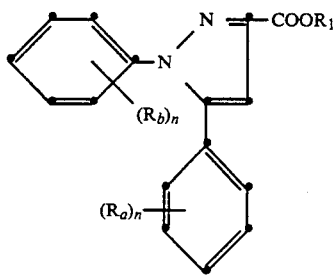

in which each of $R_a$ and $R_b$, independently of the other, represents halogen, $C_1$-$C_5$-alkyl, $C_1$-$C_5$-haloalkyl, $C_2$-$C_5$-alkenyl, $C_2$-$C_5$-alkynyl or cyano, n represents zero or an integer from 1 to 3 and $R_1$ has the meaning given above, with the proviso that, when ($R_a$) represents hydrogen, n=1 and $R_1$ represents hydrogen or ethyl, $R_b$, when it represents methyl or halogen, must be in the ortho position.

Important among these derivatives are those in which $R_a$, $R_b$ and n have the meanings given under formula I while $R_1$ represents $C_1$-$C_{18}$-alkyl or $C_3$-$C_{18}$-cycloalkyl each of which is unsubstituted or mono- or poly-substituted by $C_2$-$C_8$-alkenyl, $C_2$-$C_8$-alkynyl, $C_3$-$C_8$-cycloalkenyl, halogen, cyano, $C_1$-$C_4$-alkoxy, $C_1$-$C_4$-alkoxycarbonyl, $C_1$-$C_4$-alkylcarbonyl, carbamoyl, di($C_1$-$C_4$-alkylcarbamoyl), amino, $C_1$-$C_4$-alkylamino or by di($C_1$-$C_4$-alkylamino), or $R_1$ represents a 5- or 6-membered heterocycle Q that is bonded via N or C, or a phenyl or naphthyl radical U or an imido radical —N=C($R_2$)$R_2$, $R_2$, Q and U having the meanings given under formula I, with the proviso that, when ($R_a$)n is hydrogen, n=1 and $R_1$ is hydrogen, ($R_b$)n, when it represents methyl or halogen, must be in the ortho position.

A very good action is exhibited by the 1,5-diphenyl-pyrazole-3-carboxylic acid esters of the formula I in which $R_a$, $R_b$ and n have the meanings given under formula I while $R_1$ represents $C_1$-$C_{18}$-alkyl that is unsubstituted or mono- or poly-substituted by $C_2$-$C_8$-alkyl, $C_2$-$C_8$-alkynyl, halogen, nitro, cyano, $C_1$-$C_4$-alkoxy or by phenyl, especially the 1,5-diphenyl-pyrazole-3-carboxylic acid salts of the formula I in which $R_a$, $R_b$ and n have the meanings given under formula I and $R_1$ represents a plant-physiologically tolerable metal or ammonium cation, especially 1-(2-chlorophenyl)-3-methoxycarbonyl-5-phenylpyrazole, 1-(2,4-dichlorophenyl)-3-methoxycarbonyl-5-phenyl-pyrazole and 1-(2-chlorophenyl)-3-methoxycarbonyl-5-(2-fluorophenyl)pyrazole.

The acid halides of the 1,5-diphenylpyrazole-3-carboxylic acids of the formula I are novel and the invention relates also to these.

The 1,5-diphenylpyrazole-3-carboxylic acid derivatives of the formula I can be prepared in accordance with various methods of synthesis known per se. According to a method described in Ber. 25 3143 (1892), 3-ethoxycarbonyl-1,5-diphenylpyrazole is prepared by condensing molar amounts of bromoacetophenone and ethyl acetoacetate in the presence of sodium ethoxide to form 2-acetyl-3-benzoylpropionic acid ethyl ester to which a molar amount of phenyldiazonium chloride is added. The condensate (3-benzoyl-2-phenylhydrazinox-imepropionic acid ethyl ester) cyclises at elevated temperature to form 3-ethylcarbonyl-1,5-diphenylpyrazole. The reaction sequence can be represented schematically in the following manner:

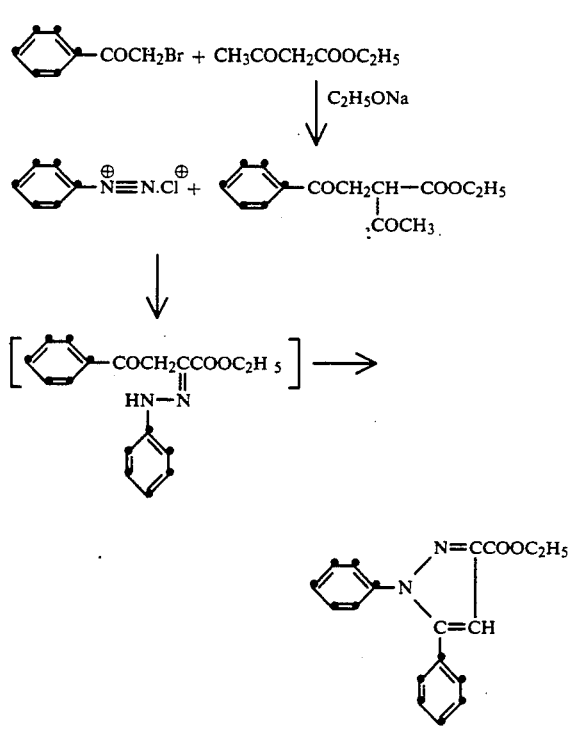

According to another process described in Ber. 47, 1435 (1914) and Can. J. Chem. 41, 1813 (1963), it is possible to prepare 1,5-diphenylpyrazole-3-carboxylic acid and its ethyl ester by mixing together molar amounts of 3-benzoylpropionic acid and acetic anhydride and adding a molar amount of a phenyldiazonium chloride to the resulting condensation product 5-phenylfuran-2-carbonyl. The resulting 2-phenylhydrazine-5-phenylfurfurylidene condensate cyclises at elevated temperature to form the 3-carboxylic acid 1,5-diphenylpyrazole or an ester thereof in accordance with the scheme

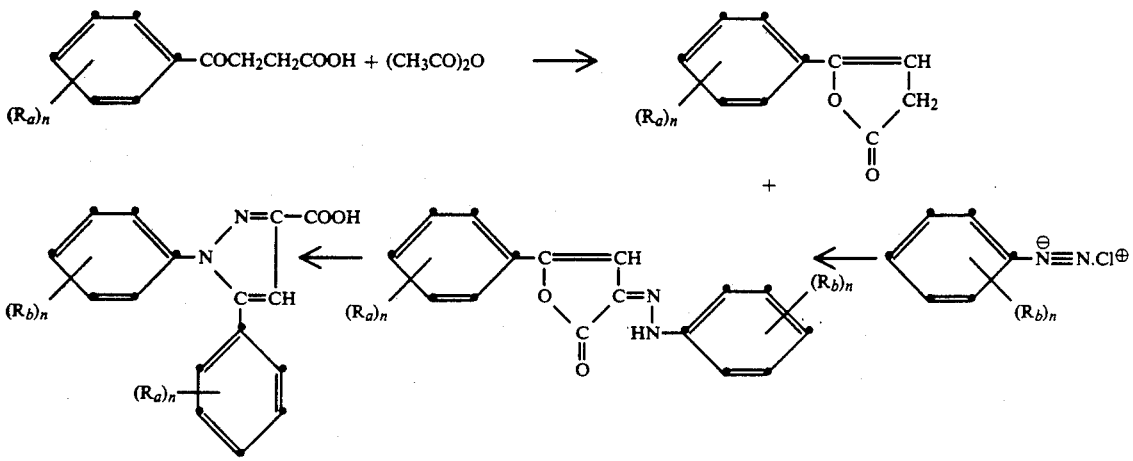

(III)

In these formulae, ($R_a$), ($R_b$), and n have the meanings given under formula I and $R_b$ represents preferably ortho chlorine or para methyl.

According to a further process analogous to Ber. 20 2185 (1887), it is possible to prepare 1,5-diphenylpyrazole-3-carboxylic acids and their esters by condensing equimolar amounts of acetophenone and oxalic acid dimethyl ester in the presence of a base, for example sodium methoxide or ethoxide, to form benzoylpyruvic acid methyl ester, adding an equimolar amount of a phenylhydrazine thereto and cyclising the condensate in an acidic medium, in accordance with the reaction scheme

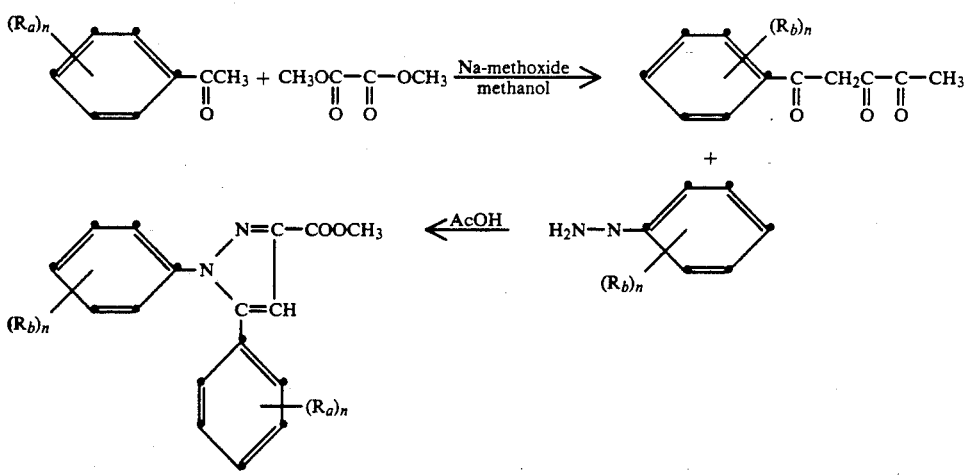

In these formulae $R_a$, $R_b$ and n have the meanings given under formula I.

The process according to the invention for the preparation of the 1,5-diphenylpyrazole 3-carboxylic acid esters is characterised in that an acetophenone of the formula III in which $R_a$ and n have the meanings given under formula I is reacted in an inert organic solvent in the presence of a base with an equimolar amount of an oxalic acid diester of the formula IV

  (IV)

in which $R_1$ has the meaning given under formula I, there is added to the resulting benzoylpyruvic acid ester of the formula V

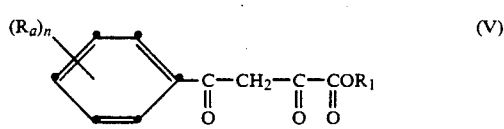  (V)

in which $R_a$, $R_1$ and n have the meanings given under formula I an equimolar amount of phenylhydrazine of the formula VI

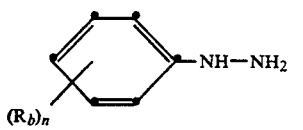

in which $R_b$ and n have the meanings given under formula I, and then the mixture is cyclised in an acidic medium at elevated temperature to form the 1,5-diphenylpyrazole-3-carboxylic acid derivative of the formula I.

Suitable inert solvents for the condensation of the acetophenone and the oxalic acid ester are the corresponding alcohols, such as methanol, ethanol or acetone, higher-boiling ketones, such as methyl ethyl ketone or dioxan, but also higher-boiling ethers, such as dipropyl ether, tetrahydrofuran, and also aromatic hydrocarbons, such as benzene, toluene and xylene.

The cyclisation of the condensate of benzoylpyruvic acid ester with the hydrazine is carried out in an acidic medium, preferably in glacial acetic acid.

The reaction temperatures are from 0° C. to 200° C. but the operation is preferably carried out at from 0° C. up to the boiling point of the reaction mixture.

The following methods of synthesis are suitable for the preparation of the esters of the 1,5-diphenylpyrazole-3-carboxylic acids of the formula I:

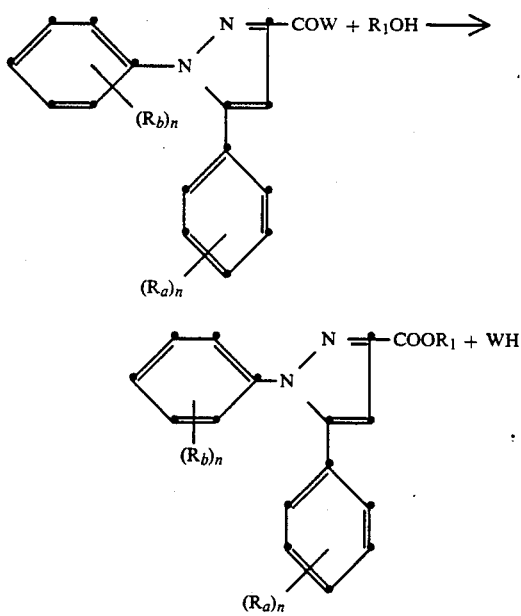

Suitable as acid derivative W are the radicals listed under 1.1 to 1.5.

1.1. Halogen or the imidazole radical

1.2. Hydroxy

These reactions run smoothly, in some cases even at room temperature, in a solvent or diluent that is inert towards the reactants. If the acid halide is used, an equimolar amount of a base is added as acid-binding agent.

When W is hydroxy, an agent for removing the elements of water, such as cyclohexyldiimide or sulphuric acid, or boiling in a water separator, is also suitable.

1.3. $C_1-C_4$-alkoxy

The reaction is carried out as an acid-catalysed or base-catalysed ester rearrangement and takes place at elevated temperature (from room to boiling temperature) in an excess of $R_1OH$, which may also serve as solvent, and in the presence of a catalytic amount of an acid or base. It is also possible to use as solvent a hydrocarbon, such as benzene, toluene or xylene, cyclohexane, an ether, such as diethyl ether, tetrahydrofuran or dioxan.

1.4. $O-CO-C_1-C_4$-alkyl

The reaction of the acid anhydrides, like that of the halides, takes place in some cases even at room temperature, in an inert solvent or diluent If necessary, an equimolar amount of a base is added as acid-binding agent.

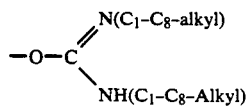

In this reaction the amidine radical splits off with the addition of a hydrogen atom as urea. This esterification takes place in an inert anhydrous solvent, advantageously in a hydrocarbon, such as benzene, toluene, xylene or cyclohexane.

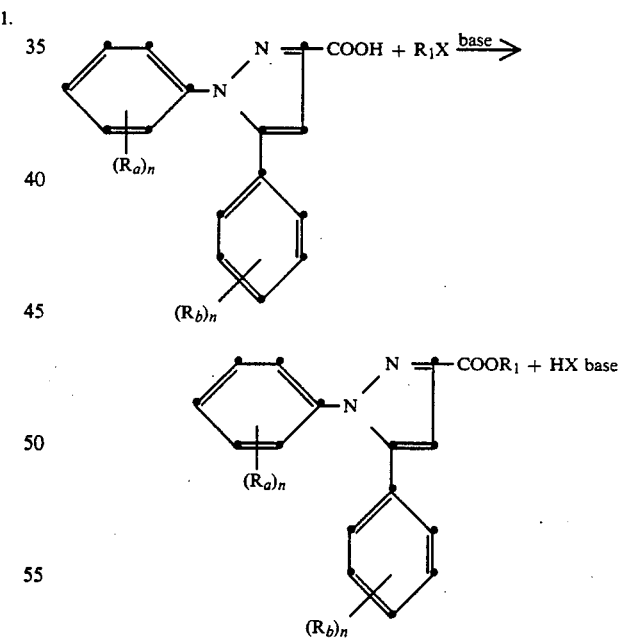

Halogen or a radical $-OSO_2(C_1-C_4$-alkyl) is suitable as X. The reaction takes place in an organic solvent or diluent, in the presence of a base, such as, for example, an alkali metal alcoholate or an alkali metal or alkaline earth metal carbonate or hydrogen carbonate. These bases should not be reactive towards R—X.

The preparation of a 1,5-diphenylpyrazole-3-carboxylic acid ester according to the invention is described in the following Example. The temperatures are given in degrees Celsius.

Examples of other 1,5-diphenylpyrazole-3-carboxylic acid derivatives of the formula I are given in Table 2.

EXAMPLE 1

Manufacture of 1-(2-chlorophenyl)-3-methoxycarbonyl-5-phenyl-pyrazole

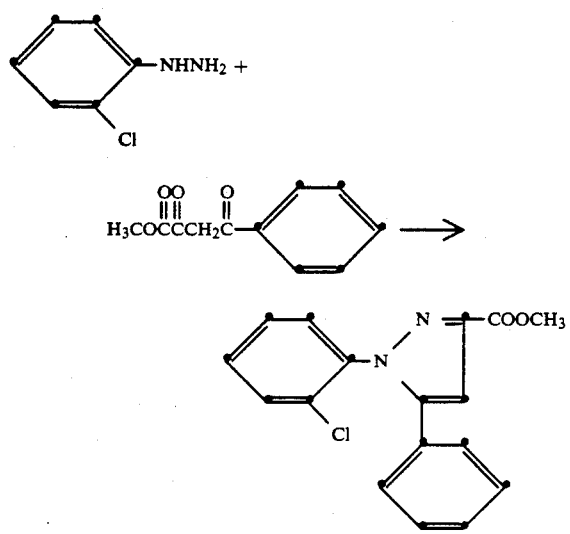

(a) 19.3 g (0.105 mol) of 2-chlorophenylhydrazine hydrochloride (97% strength) and 8.6 g (0.105 mol) of sodium acetate are added to a solution of 21.2 g (0.103 mol) of benzoylpyruvic acid methyl ester in 100 ml of glacial acetic acid. After the reaction mixture has been boiled under reflux for 2 hours, it is cooled to room temperature and then poured into ice-water. The resin formed is taken up in ethyl acetate and washed neutral with water and 1M soda solution. The organic phase is separated off, dried over sodium sulphate and concentrated in a rotary evaporator. The oil that remains is crystallised from diisopropyl ether. 17.6 g of title product having a melting point of 67°–71° are thus obtained.

The benzoylpyruvic acid methyl ester required as starting material is prepared in the following manner:

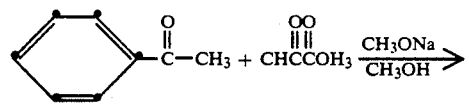

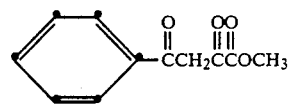

b) A mixture of 75 ml (0.405 mol) of 30% sodium methoxide solution and 30 ml of methanol is cooled to 0°, and then 48 g (0.4 mol) of acetophenone are added slowly while stirring. A solution of 47.2 g (0.4 mol) of oxalic acid dimethyl ester in 100 ml of methanol is added dropwise to the mixture while stirring at 8°–10°. The reaction mixture becomes turbid and finally a thick yellow precipitate is formed which can hardly be stirred. Sufficient methanol is added to make it possible to stir the reaction mixture again. After stirring for a further 3 hours at room temperature, the whole is filtered with suction and the precipitate is washed with diethyl ether and subjected to suction until dry. The filter material is suspended in water and adjusted to pH 4 with glacial acetic acid while stirring and cooling whereupon the benzoylpyruvic acid methyl ester is formed. It is filtered off, washed with ice-water and dried over phosphorus pentoxide in an desiccator. 42 g of ester having a melting point of 56°–58° are obtained.

EXAMPLE 2

Manufacture of 1-(2-chlorophenyl)-5-phenylpyrazole-3-carboxylic acid chloride

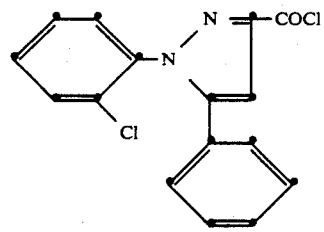

A mixture of 149.4 g of 1-(2-chlorophenyl)-5-phenyl-pyrazole-3-carboxylic acid and 2000 ml of dry ethylene chloride is heated to 70°. 40 ml of thionyl chloride are added dropwise thereto over a period of 12 minutes while stirring. The reaction mixture is then maintained at reflux temperature for 2¼ hours, cooled to room temperature and concentrated by evaporation in vacuo. The residue is recrystallised from cyclohexane/hexane 126 g of the above acid chloride, which has a melting point of 101°–102°, are thus obtained.

TABLE 2

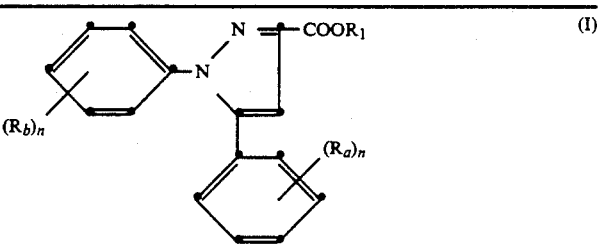

(I)

| No. | $(R_a)_n$ | $(R_b)_n$ | $R_1$ | phys. data |
|---|---|---|---|---|
| 1 | — | 2-Cl | $CH_3$ | m.p. 67–70° |
| 2 | — | 2-Cl | $C_2H_5$ | |
| 3 | — | 2-Cl | $C_3H_7$-n | |
| 4 | — | 2-Cl | $CH(CH_3)_2$ | |

TABLE 2-continued

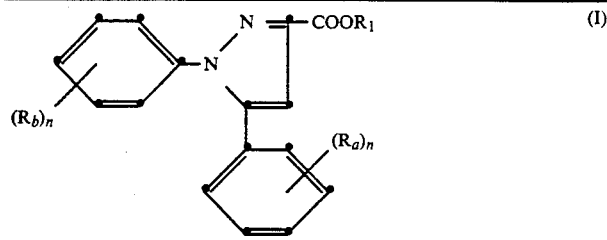

(I)

| No. | $(R_a)_n$ | $(R_b)_n$ | $R_1$ | phys. data |
|---|---|---|---|---|
| 5 | — | 2-Cl | $CH_2CH(CH_3)_2$ | |
| 6 | — | 2-Cl | Tetrahydrofurfuryl | |
| 7 | — | 2-Cl | $CH_2CH_2CH(CH_3)_2$ | |
| 8 | — | 2-Cl | $CH_2CH(C_2H_5)_2$ | |
| 9 | — | 2-Cl | $CH(CH_3)CH_2OCH_3$ | |
| 10 | — | 2-Cl | $CH_2CH_2OCH(CH_3)_2$ | |
| 11 | — | 2-Cl | $CH_2CH=CH_2$ | |
| 12 | — | 2-Cl | $CH_2C(CH_3)=CH_2$ | m.p. 66–70° |
| 13 | — | 2-Cl | $CH_2CH_2Cl$ | |
| 14 | — | 2-Cl | $CH_2CH(CH_3)CH_2CH_3$ | |
| 15 | — | 2-Cl | $CH_2C\equiv CH$ | m.p. 114–115° |
| 16 | — | 2-Cl | $CH_2CH_2C\equiv CH$ | |
| 17 | — | 2-Cl | $C(CH_3)_2CH_2CH_3$ | |
| 18 | — | 2-Cl | $CH(CH_3)COOCH_3$ | |
| 19 | — | 2-Cl | $C(CH_3)_2COOC_2H_5$ | |
| 20 | — | 2-Cl | $CH_2CH_2CN$ | |
| 21 | — | 2-Cl | Pyran-2-ylmethyl | |
| 22 | — | 2-Cl | Benzyl | m.p. 142–144° |
| 23 | — | 2-Cl | $CH_2CCl_3$ | |
| 24 | — | 2-Cl | Phenoxyethyl | m.p. 84–91° |
| 25 | — | 2-Cl | Cyclopropylmethyl | |
| 26 | — | 2-Cl | Cyclopentylmethyl | |
| 27 | — | 2-Cl | 2,2-Dimethyl-1,3-dioxolan-4-ylmethyl | |
| 28 | — | 2-Cl | 2-Thenyl | m.p. 147–149° |
| 29 | — | 2-Cl | $CH_2CH=CHCl$ | |
| 30 | — | 2-Cl | $CH_2C(Cl)=CH_2$ | |
| 31 | — | 2-Cl | $CH_2CH_2Si(CH_3)_3$ | m.p. 88–89° |
| 32 | — | 2-Cl | $CH_2Si(CH_3)_3$ | |
| 33 | — | 2-Cl | Pyrazol-1-yl-ethyl | |
| 34 | — | 2-Cl | $CH_2CH(NO_2)CH_3$ | |
| 35 | — | 2-Cl | $CH_2CH=CHCH_3$ | |
| 36 | — | 2-Cl | Cyclohexyl | m.p. 144–145° |
| 37 | — | 2-Cl | $(CH_2)_9CH_3$ | |
| 38 | — | 2-Cl | $CH_2CH_2N(C_2H_5)_2$ | |
| 39 | — | 2-Cl | $CH_2CH_2OCH_2CH_2OC_2H_5$ | |
| 40 | — | 2-Cl | $CH_2CH(Br)CH_2Br$ | |
| 41 | — | 2-Cl | $CH(CH_2Cl)_2$ | |
| 42 | — | 2-Cl | $CH_2CH_2NO_2$ | |
| 43 | — | 2-Cl | $CH_2C(CH_3)_2N(CH_3)_2$ | |
| 44 | — | 2-Cl | $CH(CH_3)CH_2N(CH_3)_2$ | |
| 45 | — | 2-Cl | 2,6-Dimethylcyclohexyl | |
| 46 | — | 2-Cl | 2-Furfuryl | |
| 47 | — | 2-Cl | Morpholinoethyl | |
| 48 | — | 2-Cl | $CH_2CN$ | |
| 49 | — | 2-Cl | Cyclohexylmethyl | m.p. 103–104° |
| 50 | — | 2-Cl | Pyrazol-1-yl-prop-2-yl | m.p. 91–92° |
| 51 | — | 2-Cl | $CH_2CH_2SO_2CH_3$ | |
| 52 | — | 2-Cl | $CH_2COOCH_3$ | m.p. 143–145° |
| 53 | — | 2-Cl | $CH(CH_3)(CH_2)_4CH_3$ | $n_D^{25}$ 1.5470 |
| 54 | — | 2-Cl | $CH(CH=CH_2)(CH_2)_4CH_3$ | |
| 55 | — | 2,4 $Cl_2$ | $CH_3$ | m.p. 140–143° |
| 56 | — | 2,4 $Cl_2$ | $C_2H_5$ | |
| 57 | — | 2,4 $Cl_2$ | $CH(CH_3)_2$ | |
| 58 | — | 2,4 $Cl_2$ | $CH(CH_3)(CH_2)_4CH_3$ | |
| 59 | — | 2,4 $Cl_2$ | $CH_2CH=CH_2$ | |
| 60 | — | 2,4 $Cl_2$ | $CH_2C\equiv CH$ | |
| 61 | — | 2,4 $Cl_2$ | Benzyl | |
| 62 | — | 2,4 $Cl_2$ | $(CH_2)_7CH_3$ | |
| 63 | — | 2,3 $Cl_2$ | $CH_3$ | |
| 64 | — | 2,3 $Cl_2$ | $C_2H_5$ | |
| 65 | — | 2,3 $Cl_2$ | $CH(CH_3)_2$ | |
| 66 | — | 2,3 $Cl_2$ | $CH(CH_3)(CH_2)_4CH_3$ | |
| 67 | — | 2,3 $Cl_2$ | $CH_2CH=CH_2$ | |
| 68 | — | 2,3 $Cl_2$ | $CH_2C\equiv CH$ | |
| 69 | — | 2,3 $Cl_2$ | Benzyl $(CH_2)_7CH_3$ | |

TABLE 2-continued

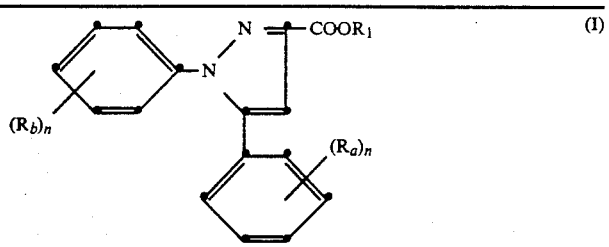

(I)

| No. | $(R_a)_n$ | $(R_b)_n$ | $R_1$ | phys. data |
|---|---|---|---|---|
| 70 | — | 2-F | $CH_3$ | m.p. 83–85° |
| 71 | — | 2-F | $C_2H_5$ | |
| 72 | — | 2-F | $CH(CH_3)_2$ | |
| 73 | — | 2-F | $CH(CH_3)(CH_2)_4CH_3$ | |
| 74 | — | 2-F | $CH_2CH=CH_2$ | |
| 75 | — | 2-F | $CH_2CH\equiv CH$ | |
| 76 | — | 2-F | Benzyl | |
| 77 | — | 2-F | $(CH_2)_7CH_3$ | |
| 78 | — | 2-$OCH_3$ | $CH_3$ | m.p. 126–128° |
| 79 | — | 2-$OCH_3$ | $C_2H_5$ | |
| 80 | — | 2-$OCH_3$ | $CH(CH_3)_2$ | |
| 81 | — | 2-$OCH_3$ | $CH(CH_3)(CH_2)_4CH_3$ | |
| 82 | — | 2-$OCH_3$ | $CH_2CH=CH_2$ | |
| 83 | — | 2-$OCH_3$ | $CH_2C\equiv CH$ | |
| 84 | — | 2-$OCH_3$ | Benzyl | |
| 85 | — | 2-$OCH_3$ | $(CH_2)_7CH_3$ | |
| 86 | — | 2,5 $Cl_2$ | $CH_3$ | |
| 87 | — | 2,5 $Cl_2$ | $C_2H_5$ | |
| 88 | — | 2,5 $Cl_2$ | $CH(CH_3)_2$ | |
| 89 | — | 2,5 $Cl_2$ | $CH(CH_3)(CH_2)_4CH_3$ | |
| 90 | — | 2,5 $Cl_2$ | $CH_2CH=CH_2$ | |
| 91 | — | 2,5 $Cl_2$ | $CH_2C\equiv CH$ | |
| 92 | — | 2,5 $Cl_2$ | Benzyl | |
| 93 | — | 2,5 $Cl_2$ | $(CH_2)_7CH_3$ | |
| 94 | — | 2-Cl, 4-$CH_3$ | $CH_3$ | |
| 95 | — | 2-Cl, 4-$CH_3$ | $C_2H_5$ | |
| 96 | — | 2-Cl, 4-$CH_3$ | $CH(CH_3)_2$ | |
| 97 | — | 2-Cl, 4-$CH_3$ | $CH(CH_3)(CH_2)_4CH_3$ | |
| 98 | — | 2-Cl, 4-$CH_3$ | $CH_2CH=CH_2$ | |
| 99 | — | 2-Cl, 4-$CH_3$ | $CH_2C\equiv CH$ | |
| 100 | — | 2-Cl, 4-$CH_3$ | Benzyl | |
| 101 | — | 2-Cl, 4-$CH_3$ | $(CH_2)_7CH_3$ | |
| 102 | — | 2-Br | $CH_3$ | m.p. 81–83° |
| 103 | — | 2-Br | $C_2H_5$ | |
| 104 | — | 2-Br | $CH(CH_3)_2$ | |
| 105 | — | 2-Br | $CH(CH_3)(CH_2)_4CH_3$ | |
| 106 | — | 2-Br | $CH_2CH=CH_2$ | |
| 107 | — | 2-Br | $CH_2C\equiv CH$ | |
| 108 | — | 2-Br | Benzyl | |
| 109 | — | 2-Br | $(CH_2)_7CH_3$ | |
| 110 | — | 2-$CH_3$ | $CH_3$ | m.p. 105–106° |
| 111 | — | 2-$CH_3$ | $C_2H_5$ | |
| 112 | — | 2-$CH_3$ | $CH(CH_3)_2$ | |
| 113 | — | 2-$CH_3$ | $CH(CH_3)(CH_2)_7CH_3$ | |
| 114 | — | 2-$CH_3$ | $CH_2CH=CH_2$ | |
| 115 | — | 2-$CH_3$ | $CH_2C\equiv CH$ | |
| 116 | — | 2-$CH_3$ | Benzyl | |
| 117 | — | 2-$CH_3$ | $(CH_2)_7CH_3$ | |
| 118 | — | 2,4 $Cl_2$, 5-$OCH_3$ | $CH_3$ | |
| 119 | — | 2,4 $Cl_2$, 5-$OCH_3$ | $C_2H_5$ | |
| 120 | — | 2,4 $Cl_2$, 5-$OCH_3$ | $CH(CH_3)_2$ | |
| 121 | — | 2,4 $Cl_2$, 5-$OCH_3$ | $CH(CH_3)(CH_2)_4CH_3$ | |
| 122 | — | 2,4 $Cl_2$, 5-$OCH_3$ | $CH_2CH=CH_2$ | |
| 123 | — | 2,4 $Cl_2$, 5-$OCH_3$ | $CH_2C\equiv CH$ | |
| 124 | — | 2,4 $Cl_2$, 5-$OCH_3$ | Benzyl | |
| 125 | — | 2,4 $Cl_2$, 5-$OCH_3$ | $(CH_2)_7CH_3$ | |
| 126 | 3-$CH_3$ | 2-Cl | $CH_3$ | m.p. 129–130° |
| 127 | 3-Cl | 2-Cl | $CH_3$ | m.p. 141–143° |
| 128 | 3-$OCH_3$ | 2-Cl | $CH_3$ | m.p. 115–117° |
| 129 | 3-F | 2-Cl | $CH_3$ | m.p. 114–116° |
| 130 | — | — | $CH_3$ | m.p. 84–85° |
| 131 | — | 2-$NO_2$ | $CH_3$ | m.p. 208–210° |
| 132 | — | — | $C_2H_5$ | m.p. 85–87° |
| 133 | — | 2-Cl | $(CH_2CH=CHCH_2)_2CH_2CH(CH_3)_2$<br>$\|$<br>$CH_3$ | |
| 134 | — | 2-Cl | $-CH_2(CH_2)_3CH=CH_2$ | $n_D^{20}$ 1.5818 |
| 135 | — | 2-Cl | 2-Chlorobenzyl | m.p. 96–98° |

TABLE 2-continued $$(I)$$

| No. | $(R_a)_n$ | $(R_b)_n$ | $R_1$ | phys. data |
|---|---|---|---|---|
| 136 | — | 2-Cl | —(CH$_2$)$_7$CH$_3$ | $n_D^{20}$ 1.5532 |
| 137 | — | 2-Cl | —(CH$_2$)$_{11}$—CH$_3$ | m.p. 66–67° |
| 138 | — | 2-Cl | 5-Chloro-2-methoxy-phenyl-ethyl | m.p. 129–130° |
| 140 | — | 2-Cl | Pyridin-3-yl | m.p. 110–111° |
| 141 | — | 2-Cl | Pyridin-2-yl | |
| 142 | — | 2-Cl | Tetrahydrofuryl-3 | m.p. 95–97° |
| 143 | — | 2-Cl | 5-Methyl-thiazol-4-ylethyl | m.p. 90–91° |
| 144 | — | 2-Cl | Thiophen-2-yl-ethyl | m.p. 123–124° |
| 145 | — | 2-Cl | —(CH$_2$)$_3$CH$_3$ | m.p. 66–68° |
| 146 | — | 2-Cl | —CH$_2$—CONH$_2$ | m.p. 192–194° |
| 147 | — | 2-Cl | —(CH$_2$)$_8$CH=CH(CH$_2$)$_7$CH$_3$ | |
| 148 | — | 2-Cl | HN$^{\oplus}$(C$_2$H$_5$)$_3$ | m.p. 163–166° |
| 149 | — | 2-Cl | H$_3$N$^{\oplus}$CH(CH$_3$)$_2$ | m.p. 165–168° |
| 150 | — | 2-Cl | 2,3.4,6.7.8.9.-10-Octahydropyrimido-[2,1-a]-azepin-1-ium | m.p. 204–206° |
| 151 | — | 2-Cl | Na$^{\oplus}$ | m.p. >260° |
| 152 | — | 2-Cl | H | m.p. 198–200° |
| 153 | — | 2-Cl | OR$_1$ = Cl (acid chloride) | m.p. 101–102° |
| 154 | — | 2-F | OR$_1$ = Cl (acid chloride) | |
| 155 | 3-F | 2-Fl | OR$_1$ = Cl (acid chloride) | |
| 156 | 2-F | — | OR$_1$ = Cl (acid chloride) | |
| 157 | 2-Cl | — | OR$_1$ = Cl (acid chloride) | |
| 158 | — | 2-CH$_3$ | OR$_1$ = Cl (acid chloride) | |
| 159 | 2-Cl | 2,4 (Cl$_2$) | CH$_3$ | m.p. 84–88° |
| 160 | 2-Cl | 2-F | CH$_3$ | m.p. 84–87° |
| 161 | 2-F | 3-OCH$_3$ | CH$_3$ | m.p. 114–115° |
| 162 | — | 3-OCH$_3$ | CH$_3$ | m.p. 103–106° |
| 163 | 2F, 4Cl SOC$_3$H$_7$iso | 3-OCH$_3$ | CH$_3$ | m.p. 82–84° |
| 164 | 2,4-Cl$_2$ | 3-OCH$_3$ | CH$_3$ | m.p. 109–111° |
| 165 | — | 2-Cl | —(CH$_2$)$_{17}$—CH$_3$ | m.p. 77–79° |
| 166 | — | 2-Cl | —(CH$_2$CH=CCH$_2$—)$_3$H<br>$\quad\quad\quad\quad$\|<br>$\quad\quad\quad\quad$CH$_3$ | $n_D^{20}$ 1.5580 |
| 167 | — | 2-Cl | —CH(CH$_2$)$_7$CH=CH(CH$_2$)$_7$CH$_3$ | $n_D^{22}$ 1.5375 |

The 1,5-diphenylpyrazole-3-carboxylic acid derivatives of the formula I according to the invention are used as safeners in admixture with 2-[4-(phenoxy, pyridin-2-yloxy, 4-benzoxazolyloxy, 4 benzothiazolyloxy and 4-quinoxalin-2-yloxy)-phenoxy]-propionic acid ester herbicides of the formula II for controlling weeds in crops of useful plants.

The weeds to be controlled may be both monocotyledonous and dicotyledenous weeds.

There come into consideration as cultivated plants or parts of those plants, for example, those mentioned above. Cultivation areas are those areas of land in which cultivated plants are already growing or in which the seeds of those cultivated plants have already been sown, and also the areas of land intended for growing those cultivated plants.

The amount of antidote to be used in relation to the herbicide depends to a large extent on the method of application. In the case of field treatment that is carried out either by using a tank mix with a combination of antidote and herbicide or by applying the antidote and the herbicide separately, the ratio of antidote to herbicide is generally from 1:100 to 10:1, preferably from 1:20 to 1:1, and especially 1:1. In contrast, in the case of seed dressing, far smaller amounts of antidote are required per hectare of land under cultivation in relation to the amount of herbicide.

In the case of field treatment, from 0.01 to 10 kg antidote/ha, preferably from 0.05 to 0.5 kg antidote/ha, are normally applied.

In the case of seed dressing, from 0.01 to 10 g antidote/kg seed, preferably from 0.05 to 2 g antidote/kg seed, are normally applied. If the antidote is applied in liquid form by soaking the seeds shortly before they are sown it is advantageous to use antidote solutions that contain the active ingredient in a concentration of from 1 to 10,000 ppm, preferably from 100 to 1000 ppm.

For application, the compounds of the formula I or combinations of compounds of the formula I with the herbicides to be antagonised are advantageously used together with the adjuvants customarily used in the art of formulation and are therefore processed in known manner to form, for example, emulsifiable concentrates, pastes that can be applied as a coating, directly sprayable or dilutable solutions, dilute emulsions, wettable powders, soluble powders, dusts, granulates, and also encapsulations in, for example, polymeric substances.

As with the nature of the compositions to be used, the methods of application, such as spraying, atomising, dusting, scattering, coating or pouring, are chosen in accordance with the intended objectives and the prevailing circumstances.

The formulations, i.e. the compositions or preparations containing the active ingredient of the formula I or a combination of the active ingredient of the formula I and the herbicide to be antagonised and, where appropriate, a solid or liquid adjuvant, are prepared in known manner, for example by intimately mixing and/or grinding the active ingredients with extenders, such as, for example, solvents, solid carriers, and, where appropriate, surface-active compounds (surfactants).

Suitable solvents are: aromatic hydrocarbons, preferably the fractions $C_8$ to $C_{12}$, such as, for example, xylene mixtures or substituted naphthalenes, phthalic acid esters, such as dibutyl or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulphoxide or dimethylformamide, and also optionally epoxidised vegetable oils, such as epoxidised coconut oil or soybean oil, or water.

The solid carriers used, for example for dusts and dispersible powders, are generally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, such as, for example, pumice, broken brick, sepiolite or bentonite, and suitable nonsorbent carriers are, for example, calcite or sand. In addition, it is possible to use a large number of pre-granulated materials of inorganic or organic nature, such as, especially, dolomite or pulverised plant residues.

Depending on the nature of the active ingredient of the formula I to be formulated and optionally also on the nature of the herbicide to be antagonised, suitable surface-active compounds are nonionic, cationic and/or anionic surfactants having good emulsifying, dispersing and wetting properties. The term "surfactants" should also be understood as meaning mixtures of surfactants.

Suitable anionic surfactants may be both so-called water-soluble soaps and water-soluble synthetic surface-active compounds.

There may be mentioned as soaps the alkali metal salts, alkaline earth metal salts and unsubstituted or substituted ammonium salts of higher fatty acids ($C_{10}$–$C_{22}$), such as, for example, the sodium or potassium sa oleic or stearic acid, or of natural fatty acid mixtures, which can be obtained, for example, from coconut or tallow oil. Fatty acid methyltaurine salts should also be mentioned.

So-called synthetic surfactants are, however, more often used, especially fatty sulphonates, fatty sulphates, sulphonated benzimidazole derivatives or alkylarylsulphonates.

The fatty sulphonates or fatty sulphates are generally in the form of alkali metal salts, alkaline earth metal salts or unsubstituted or substituted ammonium salts and have an alkyl radical having from 8 to 22 carbon atoms, alkyl also including the alkyl moiety of acyl radicals, for example the sodium or calcium salt of lignosulphonic acid, of dodecylsulphuric acid ester or of a fatty alcohol sulphate mixture produced from natural fatty acids. These also include the salts of sulphuric acid esters and sulphonic acids of fatty alcohol/ethylene oxide adducts. The sulphonated benzimidazole derivatives contain preferably 2 sulphonic acid groups and one fatty acid radical having from 8 to 22 carbon atoms. Alkylarylsulphonates are, for example, the sodium, calcium or triethanolamine salts of dodecylbenzenesulphonic acid, of dibutylnaphthalenesulphonic acid or of a naphthalenesulphonic acid/formaldehyde condensation product.

Also suitable are corresponding phosphates, such as, for example, salts of the phosphoric acid ester of an adduct of p-nonylphenol with from 4 to 14 moles of ethylene oxide, or phospholipids.

Suitable nonionic surfactants are especially polyglycol ether derivatives of aliphatic or cycloaliphatic alcohols, of saturated or unsaturated fatty acids and of alkylphenols, that may contain from 3 to 30 glycol ether groups and from 8 to 20 carbon atoms in the (aliphatic) hydrocarbon radical and from 6 to 18 carbon atoms in the alkyl radical of the alkylphenols.

Further suitable nonionic surfactants are the water-soluble adducts of polyethylene oxide with polypropylene glycol, ethylenediaminopolypropylene glycol and alkylpolypropylene glycol containing from 1 to 10 carbon atoms in the alkyl chain, which adducts contain from 20 to 250 ethylene glycol ether groups and from 10 to 100 propylene glycol ether groups. The said compounds normally contain from 1 to 5 ethylene glycol units per propylene glycol unit.

There may be mentioned as examples of nonionic surfactants nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Also suitable are fatty acid esters of polyoxyethylenesorbitan, such as polyoxyethylenesorbitan trioleate.

Cationic surfactants are especially quaternary ammonium salts that contain, as N-substituent, at least one alkyl radical having from 8 to 22 carbon atoms and, as further substituents, lower unsubstituted or halogenated alkyl, benzyl or lower hydroxyalkyl radicals. The salts are preferably in the form of halides, methyl sulphates or ethyl sulphates, for example stearyltrimethylammonium chloride or benzyldi(2-chloroethyl)ethylammonium bromide.

The surfactants customarily employed in the art of formulation are described, inter alia, in the following publications: "McCutcheon's Detergents and Emulsifiers Annual" MC Publishing Corp., Ridgewood, N.J., 1981. Stache, H., "Tensid-Taschenbuch", Carl Hanser Verlag, Munich/Vienna, 1981.

The agrochemical preparations generally contain from 0.1 to 99% by weight, especially from 0.1 to 95% by weight, active ingredient of the formula I or active ingredient mixture antidote/herbicide, from 1 to 99.9% by weight, especially from 5 to 99.8% by weight, solid or liquid adjuvant and from 0 to 25% by weight, especially from 0.1 to 25% by weight, surfactant.

Whereas commercial products will preferably be formulated as concentrates, the end user will normally employ dilute formulations.

The compositions may also contain other additives, such as stabilisers, anti-foams, viscosity regulators, binders, tackifiers and also fertilisers or other active ingredients in order to achieve special effects.

There are various suitable methods and techniques for using compounds of the formula I or compositions containing them for the protection of cultivated plants against the harmful effects of herbicides of the formula II; the following are examples:

i) Seed Dressing a) Dressing the seeds with an active ingredient of formula I, formulated as a wettable powder, by agitating in a vessel until uniformly distributed on the seed surface (dry dressing). Approximately from 1 to 500 g of active ingredient of formula I (from 4 g to 2 kg of wettable powder) are used per 100 kg of seeds.

b) Dressing the seeds with an emulsifiable concentrate of the active ingredient of formula I according to method a) (wet dressing).

c) Dressing by immersing the seeds in a liquor containing 50–3200 ppm of active ingredient of formula I for from 1 to 72 hours and, if desired, subsequently drying the seeds (immersion dressing).

Dressing the seeds or treating the germinated seedlings are naturally the preferred methods of application because the treatment with the active ingredient is directed exclusively at the target crop. Generally, from 1 to 500 g of antidote, preferably from 5 to 250 g of antidote, are used per 100 kg of seeds, but the amount may be higher or lower than the limit concentrations specified depending on the methodology, which also allows the addition of other active ingredients or micronutrients (repeat dressing).

ii) Application from a Tank Mix

A liquid preparation produced from a mixture of antidote and herbicide (quantitative ratio from 10:1 to 1:100) is used, the rate of application of herbicide being from 0.1 to 10 kg per hectare. Such a tank mix is applied before or after sowing.

iii) Application in the Seed Furrow

The antidote is introduced into the open sown seed furrow in the form of an emulsifiable concentrate, wettable powder or granulate and, after the seed furrow has been covered, the herbicide is applied in the normal manner in the pre-emergence process.

iv) Controlled Release of Active Ingredient

The active ingredient of formula I is applied in solution onto mineral granulated carriers or polymerised granulates (urea/formaldehyde) and left to dry. If desired, a coating may be applied (coated granulates) which makes it possible to release the active ingredient in controlled amounts over a predetermined period of time.

Formulation Examples for Liquid Active Ingredients of the Formula I (% = per cent by weight)

| 1. Emulsifiable concentrates | (a) | (b) | (c) |
|---|---|---|---|
| active ingredient from Table 2 | 25% | 40% | 50% |
| calcium dodecylbenzenesulphonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2. Solutions | (a) | (b) | (c) | (d) |
|---|---|---|---|---|
| active ingredient from Table 2 | 80% | 10% | 5% | 95% |
| ethylene glycol monomethyl ether | 20% | — | — | — |
| polyethylene glycol MW 400 | — | 70% | — | — |
| N-methyl-2-pyrrolidone | — | 20% | — | — |
| epoxidised coconut oil | — | — | 1% | 5% |
| benzine (boiling range 160–190° C.) | — | — | 94% | — |

The solutions are suitable for use in the form of extremely fine droplets.

| 3. Granulates | (a) | (b) |
|---|---|---|
| active ingredient from Table 2 | 5% | 10% |
| kaolin | 94% | — |
| highly dispersed silicic acid | 1% | — |
| attapulgite | — | 90% |

The active ingredient is dissolved in methylene chloride, sprayed onto the carrier and the solvent is then evaporated off in vacuo.

| 4. Dusts | (a) | (b) |
|---|---|---|
| active ingredient from Table 2 | 2% | 5% |
| highly dispersed silicic acid | 1% | 5% |
| talcum | 97% | — |
| kaolin | — | 90% |

Dusts that are ready for use are obtained by ultimately mixing the carriers with the active ingredient.

Formulation Examples for Solid Active Ingredients of the Formula I (% = per cent by weight)

| 5. Wettable powders | (a) | (b) | (c) |
|---|---|---|---|
| active ingredient from Table 2 | 25% | 50% | 75% |
| sodium lignosulphonate | 5% | 5% | — |
| sodium lauryl sulphate | 3% | — | 5% |
| sodium diisobutylnaphthalene-sulphonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is mixed well with the additives and thoroughly grounded in a suitable mill Wettable powders are obtained which can be diluted with water to form suspensions of any desired concentration.

| 6. Emulsifiable concentrate | |
|---|---|
| active ingredient from Table 2 | 10% |
| octylphenolpolyethylene glycol ether (4–5 mols of ethylene oxide) | 3% |
| calcium dodecylbenzenesulphonate | 3% |
| castor oil polyglycol ether (35 mols of ethylene oxide) | 4% |
| cyclohexanone | 30% |
| xylene mixture | 50% |

Emulsions of any desired concentration can be prepared from this concentrate by dilution with water.

| 7. Dusts | (a) | (b) |
|---|---|---|
| active ingredient from Table 2 | 5% | 8% |
| talcum | 95% | — |
| kaolin | — | 92% |

Dusts that are ready for use are obtained by mixing the active ingredient with the carriers and grinding in a suitable mill.

| 8. Extruder granulate | |
|---|---|
| active ingredient from Table 2 | 10% |
| sodium lignosulphonate | 2% |
| carboxymethylcellulose | 1% |
| kaolin | 87% |

The active ingredient is mixed with the additives, ground and moistened with water. This mixture is extruded and then dried in an air stream.

| 9. Coated granulate | |
|---|---|
| active ingredient from Table 2 | 3% |
| polyethylene glycol (MW 200) | 3% |
| kaolin | 94% |

The finely ground active ingredient is uniformly applied in a mixer to the kaolin moistened with polyethylene glycol. A dust-free coated granulate is obtained in this manner.

| 10. Suspension concentrate | |
|---|---|
| active ingredient from Table 2 | 40% |
| ethylene glycol | 10% |
| nonylphenolpolyethylene glycol ether (15 mols of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. In this manner, a suspension concentrate is obtained from which suspensions of any desired concentration can be prepared by dilution with water.

Formulation Examples for Active Ingredient Mixtures (Liquid) (%=per cent by weight)

| 11. Emulsifiable concentrates | (a) | (b) | (c) |
|---|---|---|---|
| active ingredient mixture: antidote from Table 2 and a herbicide from Table 1 in a ratio of 1:1 | 25% | 40% | 50% |
| calcium dodecylbenzenesulphonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any desired concentration can be produced from such concentrations by dilution with water.

| 12. Emulsifiable concentrates | (a) | (b) | (c) |
|---|---|---|---|
| active ingredient mixture: antidote from Table 2 and a herbicide from Table 1 in a ratio of 1:3 | 25% | 40% | 50% |
| calcium dodecylbenzenesulphonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 13. Emulsifiable concentrates | (a) | (b) | (c) |
|---|---|---|---|
| active ingredient mixture: antidote from Table 2 and a herbicide from Table 1 in a ratio of 2:1 | 25% | 40% | 50% |
| calcium dodecylbenzenesulphonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 14. Emulsifiable concentrates | (a) | (b) | (c) |
|---|---|---|---|
| active ingredient mixture: antidote from Table 2 and 2-[4-(5-chloro-3-fluoro-pyridin-2-yloxy)-phenoxy]-propionic acid methyl ester in a ratio of 1:1 | 25% | 40% | 50% |
| calcium dodecylbenzenesulphonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 15. Emulsifiable concentrates | (a) | (b) | (c) |
|---|---|---|---|
| active ingredient mixture: antidote from Table 2 and 2-[4-(5-chloro-3-fluoro-pyridin-2-yloxy)-phenoxy]-propionic acid methyl ester in a ratio of 1:3 | 25% | 40% | 50% |
| calcium dodecylbenzenesulphonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 16. Solutions | (a) | (b) | (c) | (d) |
|---|---|---|---|---|
| active ingredient mixture: antidote from Table 2 and a herbicide from Table 1 in a ratio of 1:4 | 80% | 10% | 5% | 95% |
| ethylene glycol monomethyl ether | 20% | — | — | — |
| polyethylene glycol MW 400 | — | 70% | — | — |
| N-methyl-2-pyrrolidone | — | 20% | — | — |
| epoxidised coconut oil | — | — | 1% | 5% |

| 16. Solutions | (a) | (b) | (c) | (d) |
|---|---|---|---|---|
| benzine (boiling range 160-190° C.) | — | — | 94% | — |

The solutions are suitable for use in the form of extremely fine droplets.

| 17. Solutions | (a) | (b) | (c) | (d) |
|---|---|---|---|---|
| active ingredient mixture: antidote from Table 2 and a herbicide from Table 1 in a ratio of 5:2 | 80% | 10% | 5% | 95% |
| ethylene glycol monomethyl ether | 20% | — | — | — |
| polyethylene glycol MW 400 | — | 70% | — | — |
| N-methyl-2-pyrrolidone | — | 20% | — | — |
| epoxidised coconut oil | — | — | 1% | 5% |
| benzine (boiling range 160-190° C.) | — | — | 94% | — |

The solutions are suitable for use in the form of extremely fine droplets.

| 18. Solutions | (a) | (b) | (c) | (d) |
|---|---|---|---|---|
| active ingredient mixture: antidote from Table 2 and a herbicide from Table 1 in a ratio of 1:1 | 80% | 10% | 5% | 95% |
| ethylene glycol monomethyl ether | 20% | — | — | — |
| polyethylene glycol MW 400 | — | 70% | — | — |
| N-methyl-2-pyrrolidone | — | 20% | — | — |
| epoxidised coconut oil | — | — | 1% | 5% |
| benzine (boiling range 160-190° C.) | — | — | 94% | — |

The solutions are suitable for use in the form of extremely fine droplets.

| 19. Solutions | a) | b) | c) | d) |
|---|---|---|---|---|
| active ingredient mixture: antidote from Table 2 and 2-[4-(5-chloro-3-fluoropyridin-2-yloxy)-phenoxy]-propionic acid methyl ester in a ratio of 1:1 | 80% | 10% | 5% | 95% |
| ethylene glycol monomethyl ether | 20% | — | — | — |
| polyethylene glycol MW 400 | — | 70% | — | — |
| N-methyl-2-pyrrolidone | — | 20% | — | — |
| epoxidised coconut oil | — | — | 1% | 5% |
| benzine (boiling range 160-190° C.) | — | — | 94% | — |

The solutions are suitable for use in the form of extremely fine droplets.

| 20. Solutions | a) | b) | c) | d) |
|---|---|---|---|---|
| active ingredient mixture: antidote from Table 2 and 2-[4-(5-chloro-3-fluoropyridin-2-yloxy)-phenoxy]-propionic acid methyl ester in a ratio of 1:4 | 80% | 10% | 5% | 95% |
| ethylene glycol monomethyl ether | 20% | — | — | — |
| polyethylene glycol MW 400 | — | 70% | — | — |
| N-methyl-2-pyrrolidone | — | 20% | — | — |
| epoxidised coconut oil | — | — | 1% | 5% |
| benzine (boiling range 160-190° C.) | — | — | 94% | — |

The solutions are suitable for use in the form of extremely fine droplets.

| 21. Granulates | a) | b) |
|---|---|---|
| active ingredient mixture: antidote from Table 2 and a herbicide from Table 1 in a ratio of 1:1 | 5% | 10% |
| kaolin | 94% | — |
| highly dispersed silicic acid | 1% | — |
| attapulgite | — | 90% |

The active ingredient is dissolved in methylene chloride, sprayed onto the carrier and the solvent is then evaporated off in vacuo.

| 22. Granulates | a) | b) |
|---|---|---|
| active ingredient mixture: antidote from Table 2 and 2-[4-(5-chloro-3-fluoropyridin-2-yloxy)-phenoxy]-propionic acid methyl ester in a ratio of 1:1 | 5% | 10% |
| kaolin | 94% | — |
| highly dispersed silicic acid | 1% | — |
| attapulgite | — | 90% |

The active ingredient is dissolved in methylene chloride, sprayed onto the carrier and the solvent is then evaporated off in vacuo.

| 23. Dusts | a) | b) |
|---|---|---|
| active ingredient mixture: antidote from Table 2 and a herbicide from Table 2 in a ratio of 1:1 | 2% | 5% |
| highly dispersed silicic acid | 1% | 5% |
| talcum | 97% | — |
| kaolin | — | 90% |

Dusts that are ready for use are obtained by ultimately mixing the carriers with the active ingredient.

Formulation Examples for Active Ingredient Mixtures (Solid) (%=per cent by weight)

| 24. Wettable powders | a) | b) | c) |
|---|---|---|---|
| active ingredient mixture: antidote from Table 2 and a herbicide from Table 1 in a ratio of 1:1 | 25% | 50% | 75% |
| sodium lignosulphonate | 5% | 5% | — |
| sodium lauryl sulphate | 3% | — | 5% |
| sodium diisobutylnaphthalene-sulphonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is mixed well with the additives and thoroughly ground in a suitable mill. Wettable powders are obtained which can be diluted with water to form suspensions of any desired concentration.

| 25. Wettable powders | a) | b) | c) |
|---|---|---|---|
| active ingredient mixture: antidote from Table 2 and a herbicide from Table 1 in a ratio of 1:4 | 25% | 50% | 75% |
| sodium lignosulphonate | 5% | 5% | — |
| sodium lauryl sulphate | 3% | — | 5% |
| sodium diisobutylnaphthalene-sulphonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is mixed well with the additives and thoroughly ground in a suitable mill. Wettable powders are obtained which can be diluted with water to form suspensions of any desired concentration.

| 26. Wettable powders | a) | b) | c) |
|---|---|---|---|
| active ingredient mixture: antidote from Table 2 and a herbicide from Table 1 in a ratio of 3:1 | 25% | 50% | 75% |
| sodium lignosulphonate | 5% | 5% | — |
| sodium lauryl sulphate | 3% | — | 5% |
| sodium diisobutylnaphthalene-sulphonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is mixed well with the additives and thoroughly ground in a suitable mill. Wettable powders are obtained which can be diluted with water to form suspensions of any desired concentration.

| 27. Emulsifiable concentrate | |
|---|---|
| active ingredient mixture: antidote from Table 2 and a herbicide from Table 1 in a ratio of 1:1 | 10% |
| octylphenolpolyethylene glycol ether (4-5 mols of ethylene oxide) | 3% |
| calcium dodecylbenzenesulphonate | 3% |
| castor oil polyglycol ether (35 mols of ethylene oxide) | 4% |
| cyclohexanone | 30% |
| xylene mixture | 50% |

Emulsions of any desired concentration can be prepared from this concentrate by dilution with water.

| 28. Emulsifiable concentrate | |
|---|---|
| active ingredient mixture: antidote from Table 2 and a herbicide from Table 1 in a ratio of 5:2 | 10% |
| octylphenolpolyethylene glycol ether (4-5 mols of ethylene oxide) | 3% |
| calcium dodecylbenzenesulphonate | 3% |
| castor oil polyglycol ether (35 mols of ethylene oxide) | 4% |
| cyclohexanone | 30% |
| xylene mixture | 50% |

Emulsions of any desired concentration can be prepared from this concentrate by dilution with water.

| 29. Emulsifiable concentrate | |
|---|---|
| active ingredient mixture: antidote from Table 2 and a herbicide from Table 1 in a ratio of 1:4 | 10% |
| octylphenolpolyethylene glycol ether (4-5 mols of ethylene oxide) | 3% |
| calcium dodecylbenzenesulphonate | 3% |
| castor oil polyglycol ether (35 mols of ethylene oxide) | 4% |
| cyclohexanone | 30% |
| xylene mixture | 50% |

Emulsions of any desired concentration can be prepared from this concentrate by dilution with water.

| 30. Dusts | a) | b) |
|---|---|---|
| active ingredient mixture: antidote from Table 2 and a herbicide from Table 1 in a ratio of 1:1 | 5% | 8% |
| talcum | 95% | — |
| kaolin | — | 92% |

Dusts that are ready for use are obtained by mixing the active ingredient with the carriers and grinding in a suitable mill.

| 31. Extruder granulate | |
|---|---|
| active ingredient mixture: antidote from Table 2 and a herbicide from Table 1 in a ratio of 1:1 | 10% |
| sodium lignosulphonate | 2% |
| carboxymethylcellulose | 1% |
| kaolin | 87% |

The active ingredient is mixed with the additives, ground and moistened with water. This mixture is extruded and then dried in an air stream.

| 32. Coated granulate | |
|---|---|
| active ingredient mixture: antidote from Table 2 and a herbicide from Table 1 in a ratio of 1:1 | 3% |
| polyethylene glycol (MW 200) | 3% |
| kaolin | 94% |

The finely ground active ingredient is uniformly applied in a mixer to the kaolin moistened with polyethylene glycol. A dust-free coated granulate is obtained in this manner.

| 33. Suspension concentrate | |
|---|---|
| active ingredient mixture: antidote from Table 2 and a herbicide from Table 1 in a ratio of 1:1 | 40% |
| ethylene glycol | 10% |
| nonylphenolpolyethylene glycol ether (15 mols of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. In this manner, a suspension concentrate is obtained from which suspensions of any desired concentration can be prepared by dilution with water.

| 34. Suspension concentrate | |
|---|---|
| active ingredient mixture: antidote from Table 2 and a herbicide from Table 1 in a ratio of 1:4 | 40% |
| ethylene glycol | 10% |
| nonylphenolpolyethylene glycol ether (15 mols of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% | concentrate is obtained from which suspensions of any desired concentration can be prepared by dilution with water.

| 35. Suspension concentrate | |
|---|---|
| active ingredient mixture: antidote from Table 2 and a herbicide from Table 1 in a ratio of 3:1 | 40% |
| ethylene glycol | 10% |
| nonylphenolpolyethylene glycol ether (15 mols of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. In this manner, a suspension concentrate is obtained from which suspensions of any desired concentration can be prepared by dilution with water.

BIOLOGICAL EXAMPLE

Test Description

In a greenhouse, seeds of the plants to be tested are placed in plastics pots containing 0.5 l of soil. When the plants have reached the 2- to 3-leaf stage, a safener of formula I and a herbicide of formula II are applied together in the form of a tank mix. 21 days after the application the condition of the plants is evaluated and the protective action of the safener is assessed. The assessment is based on the difference between the damage caused by the herbicide to a plant that has not been treated with the safener and the damage caused by the herbicide to a plant that has been treated with safener. The protective action is given as a percentage.

The results are given in the Table below.

Results:
Crop: Spring-sown wheat "Besso"
Herbicide:
2(R)-2-[4-(5-chloro-3-fluoropyridin-2-yloxy)-phenoxy]-propionic acid propargyl ester (Table 1, 2.19 2R-enantiomer)

| rate of application of herbicide | antidote No. (Table 2) | rate of application | protective action |
|---|---|---|---|
| 400 g/ha | 001 | 400 g/ha | 75% |
| | | 200 g/ha | 75% |
| | | 100 g/ha | 75% |
| | | 50 g/ha | 75% |
| 200 g/ha | 001 | 400 g/ha | 63% |
| | | 200 g/ha | 75% |
| | | 100 g/ha | 63% |
| | | 50 g/ha | 75% |
| 100 g/ha | 001 | 400 g/ha | 50% |
| | | 200 g/ha | 63% |
| | | 100 g/ha | 63% |
| | | 50 g/ha | 63% |
| 400 g/ha | 012 | 400 g/ha | 88% |
| | | 200 g/ha | 75% |
| | | 100 g/ha | 75% |
| | | 50 g/ha | 75% |
| 200 g/ha | 012 | 400 g/ha | 75% |
| | | 200 g/ha | 75% |
| | | 100 g/ha | 63% |
| | | 50 g/ha | 63% |
| 100 g/ha | 012 | 400 g/ha | 50% |
| | | 200 g/ha | 63% |
| | | 100 g/ha | 63% |
| | | 50 g/ha | 63% |
| 400 g/ha | 024 | 400 g/ha | 88% |

-continued

Results:
Crop: Spring-sown wheat "Besso"
Herbicide:
2(R)-2-[4-(5-chloro-3-fluoropyridin-2-yloxy)-phenoxy]-propionic acid propargyl ester (Table 1, 2.19 2R-enantiomer)

| rate of application of herbicide | antidote No. (Table 2) | rate of application | protective action |
|---|---|---|---|
| | | 200 g/ha | 88% |
| | | 100 g/ha | 88% |
| | | 50 g/ha | 75% |
| 200 g/ha | 024 | 400 g/ha | 75% |
| | | 200 g/ha | 75% |
| | | 100 g/ha | 75% |
| | | 50 g/ha | 75% |
| 100 g/ha | 024 | 400 g/ha | 63% |
| | | 200 g/ha | 63% |
| | | 100 g/ha | 63% |
| | | 50 g/ha | 63% |
| 400 g/ha | 036 | 400 g/ha | 50% |
| | | 200 g/ha | 50% |
| | | 100 g/ha | 50% |
| | | 50 g/ha | 38% |
| 200 g/ha | 036 | 400 g/ha | 63% |
| | | 200 g/ha | 75% |
| | | 100 g/ha | 75% |
| | | 50 g/ha | 50% |
| 100 g/ha | 036 | 400 g/ha | 50% |
| | | 200 g/ha | 50% |
| | | 100 g/ha | 63% |
| | | 50 g/ha | 50% |
| 400 g/ha | 049 | 400 g/ha | 63% |
| | | 200 g/ha | 63% |
| | | 100 g/ha | 63% |
| | | 50 g/ha | 38% |
| 200 g/ha | 049 | 400 g/ha | 75% |
| | | 200 g/ha | 88% |
| | | 100 g/ha | 75% |
| | | 50 g/ha | 75% |
| 100 g/ha | 049 | 400 g/ha | 50% |
| | | 200 g/ha | 63% |
| | | 100 g/ha | 63% |
| | | 50 g/ha | 50% |
| 400 g/ha | 050 | 400 g/ha | 63% |
| | | 200 g/ha | 63% |
| | | 100 g/ha | 50% |
| | | 50 g/ha | 50% |
| 200 g/ha | 050 | 400 g/ha | 63% |
| | | 200 g/ha | 75% |
| | | 100 g/ha | 75% |
| | | 50 g/ha | 63% |
| 100 g/ha | 050 | 400 g/ha | 50% |
| | | 200 g/ha | 50% |
| | | 100 g/ha | 63% |
| | | 50 g/ha | 38% |
| 400 g/ha | 052 | 400 g/ha | 88% |
| | | 200 g/ha | 75% |
| | | 100 g/ha | 75% |
| | | 50 g/ha | 88% |
| 200 g/ha | 052 | 400 g/ha | 75% |
| | | 200 g/ha | 75% |
| | | 100 g/ha | 75% |
| | | 50 g/ha | 75% |
| 100 g/ha | 052 | 400 g/ha | 63% |
| | | 200 g/ha | 63% |
| | | 100 g/ha | 63% |
| | | 50 g/ha | 63% |
| 400 g/ha | 055 | 400 g/ha | 50% |
| | | 200 g/ha | 50% |
| | | 100 g/ha | 50% |
| | | 50 g/ha | 50% |
| 200 g/ha | 055 | 400 g/ha | 63% |
| | | 200 g/ha | 63% |
| | | 100 g/ha | 75% |
| | | 50 g/ha | 63% |
| 100 g/ha | 055 | 400 g/ha | 63% |
| | | 200 g/ha | 63% |
| | | 100 g/ha | 63% |
| | | 50 g/ha | 63% |
| 400 g/ha | 070 | 400 g/ha | 63% |
| | | 200 g/ha | 63% |

-continued

Results:
Crop: Spring-sown wheat "Besso"
Herbicide:
2(R)-2-[4-(5-chloro-3-fluoropyridin-2-yloxy)-phenoxy]-
propionic acid propargyl ester (Table 1, 2.19 2R-enantiomer)

(Table 2)

| rate of application of herbicide | antidote No. | rate of application | protective action |
|---|---|---|---|
| 200 g/ha | 070 | 100 g/ha | 50% |
|  |  | 50 g/ha | 80% |
|  |  | 400 g/ha | 63% |
|  |  | 200 g/ha | 75% |
|  |  | 100 g/ha | 75% |
| 100 g/ha | 070 | 50 g/ha | 63% |
|  |  | 400 g/ha | 50% |
|  |  | 200 g/ha | 63% |
|  |  | 100 g/ha | 50% |
| 400 g/ha | 102 | 50 g/ha | 63% |
|  |  | 400 g/ha | 63% |
|  |  | 200 g/ha | 75% |
|  |  | 100 g/ha | 63% |
| 200 g/ha | 102 | 50 g/ha | 50% |
|  |  | 400 g/ha | 63% |
|  |  | 200 g/ha | 63% |
|  |  | 100 g/ha | 75% |
| 100 g/ha | 102 | 50 g/ha | 75% |
|  |  | 400 g/ha | 50% |
|  |  | 200 g/ha | 50% |
|  |  | 100 g/ha | 50% |
| 400 g/ha | 129 | 50 g/ha | 50% |
|  |  | 400 g/ha | 63% |
|  |  | 200 g/ha | 63% |
|  |  | 100 g/ha | 63% |
| 200 g/ha | 129 | 50 g/ha | 50% |
|  |  | 400 g/ha | 63% |
|  |  | 200 g/ha | 63% |
|  |  | 100 g/ha | 75% |
| 100 g/ha | 129 | 50 g/ha | 50% |
|  |  | 400 g/ha | 50% |
|  |  | 200 g/ha | 50% |
|  |  | 100 g/ha | 50% |
| 400 g/ha | 132 | 50 g/ha | 50% |
|  |  | 400 g/ha | 75% |
|  |  | 200 g/ha | 63% |
|  |  | 100 g/ha | 50% |
| 200 g/ha | 132 | 50 g/ha | 38% |
|  |  | 400 g/ha | 63% |
|  |  | 200 g/ha | 75% |
|  |  | 100 g/ha | 63% |
| 100 g/ha | 132 | 50 g/ha | 63% |
|  |  | 400 g/ha | 63% |
|  |  | 200 g/ha | 63% |
|  |  | 100 g/ha | 63% |
| 400 g/ha | 134 | 50 g/ha | 63% |
|  |  | 400 g/ha | 75% |
|  |  | 200 g/ha | 63% |
|  |  | 100 g/ha | 63% |
| 200 g/ha | 134 | 50 g/ha | 38% |
|  |  | 400 g/ha | 75% |
|  |  | 200 g/ha | 75% |
|  |  | 100 g/ha | 75% |
| 100 g/ha | 134 | 50 g/ha | 63% |
|  |  | 400 g/ha | 50% |
|  |  | 200 g/ha | 63% |
|  |  | 100 g/ha | 50% |
| 400 g/ha | 135 | 50 g/ha | 50% |
|  |  | 400 g/ha | 88% |
|  |  | 200 g/ha | 88% |
|  |  | 100 g/ha | 88% |
|  |  | 50 g/ha | 88% |
| 200 g/ha | 135 | 400 g/ha | 75% |
|  |  | 200 g/ha | 75% |
|  |  | 100 g/ha | 75% |
|  |  | 50 g/ha | 75% |
| 100 g/ha | 135 | 400 g/ha | 63% |
|  |  | 200 g/ha | 63% |
|  |  | 100 g/ha | 63% |
|  |  | 50 g/ha | 63% |
| 400 g/ha | 136 | 400 g/ha | 88% |
|  |  | 200 g/ha | 88% |
|  |  | 100 g/ha | 88% |
|  |  | 50 g/ha | 88% |
| 200 g/ha | 136 | 400 g/ha | 75% |
|  |  | 200 g/ha | 75% |
|  |  | 100 g/ha | 75% |
|  |  | 50 g/ha | 75% |
| 100 g/ha | 136 | 400 g/ha | 63% |
|  |  | 200 g/ha | 63% |
|  |  | 100 g/ha | 63% |
|  |  | 50 g/ha | 63% |
| 400 g/ha | 140 | 400 g/ha | 63% |
|  |  | 200 g/ha | 63% |
|  |  | 100 g/ha | 38% |
|  |  | 50 g/ha | 25% |
| 200 g/ha | 140 | 400 g/ha | 63% |
|  |  | 200 g/ha | 63% |
|  |  | 100 g/ha | 63% |
|  |  | 50 g/ha | 63% |
| 100 g/ha | 140 | 400 g/ha | 38% |
|  |  | 200 g/ha | 50% |
|  |  | 100 g/ha | 50% |
|  |  | 50 g/ha | 38% |
| 400 g/ha | 143 | 400 g/ha | 63% |
|  |  | 200 g/ha | 63% |
|  |  | 100 g/ha | 50% |
|  |  | 50 g/ha | 38% |
| 200 g/ha | 143 | 400 g/ha | 75% |
|  |  | 200 g/ha | 63% |
|  |  | 100 g/ha | 63% |
|  |  | 50 g/ha | 38% |
| 100 g/ha | 143 | 400 g/ha | 38% |
|  |  | 200 g/ha | 50% |
|  |  | 100 g/ha | 50% |
|  |  | 50 g/ha | 50% |
| 400 g/ha | 144 | 400 g/ha | 38% |
|  |  | 200 g/ha | 25% |
|  |  | 100 g/ha | 38% |
|  |  | 50 g/ha | 38% |
| 200 g/ha | 144 | 400 g/ha | 63% |
|  |  | 200 g/ha | 63% |
|  |  | 100 g/ha | 63% |
|  |  | 50 g/ha | 63% |
| 100 g/ha | 144 | 400 g/ha | 38% |
|  |  | 200 g/ha | 50% |
|  |  | 100 g/ha | 50% |
|  |  | 50 g/ha | 50% |
| 400 g/ha | 149 | 400 g/ha | 50% |
|  |  | 200 g/ha | 38% |
|  |  | 100 g/ha | 38% |
|  |  | 50 g/ha | 25% |
| 200 g/ha | 149 | 400 g/ha | 63% |
|  |  | 200 g/ha | 63% |
|  |  | 100 g/ha | 63% |
|  |  | 50 g/ha | 38% |
| 100 g/ha | 149 | 400 g/ha | 50% |
|  |  | 200 g/ha | 38% |
|  |  | 100 g/ha | 38% |
|  |  | 50 g/ha | 25% |
| 400 g/ha | 152 | 400 g/ha | 75% |
|  |  | 200 g/ha | 75% |
|  |  | 100 g/ha | 75% |
|  |  | 50 g/ha | 50% |
| 200 g/ha | 152 | 400 g/ha | 75% |
|  |  | 200 g/ha | 75% |
|  |  | 100 g/ha | 75% |
|  |  | 50 g/ha | 63% |
| 100 g/ha | 152 | 400 g/ha | 63% |
|  |  | 200 g/ha | 63% |
|  |  | 100 g/ha | 63% |
|  |  | 50 g/ha | 50% |
| 400 g/ha | 160 | 400 g/ha | 63% |
|  |  | 200 g/ha | 75% |
|  |  | 100 g/ha | 75% |
|  |  | 50 g/ha | 63% |

-continued

Results:
Crop: Spring-sown wheat "Besso"
Herbicide:
2(R)-2-[4-(5-chloro-3-fluoropyridin-2-yloxy)-phenoxy]-
propionic acid propargyl ester (Table 1, 2.19 2R-enantiomer)

(Table 2)

| rate of application of herbicide | antidote No. | rate of application | protective action |
|---|---|---|---|
| 200 g/ha | 160 | 400 g/ha | 75% |
|  |  | 200 g/ha | 75% |
|  |  | 100 g/ha | 75% |
|  |  | 50 g/ha | 63% |
| 100 g/ha | 160 | 400 g/ha | 50% |
|  |  | 200 g/ha | 50% |
|  |  | 100 g/ha | 50% |
|  |  | 50 g/ha | 50% |

We claim:

1. A method for protecting useful crops from the phytotoxic activity of a herbicide applied to the crops or their environs in which the herbicide is a phenyoxy-propionic acid of the formula:

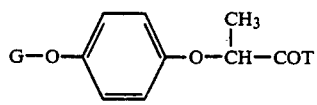

in which G is

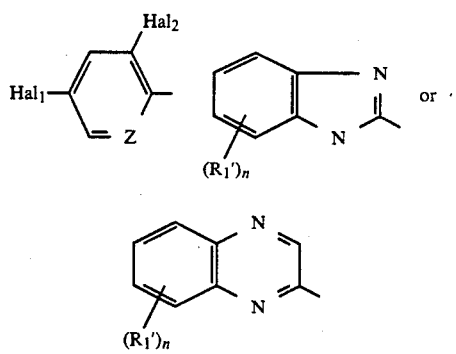

in which Hal$_1$ is a fluoro, chloro, bromo, iodo or trifluoromethyl;

Hal$_2$ is hydrogen, fluoro, chloro, bromo or trifluoromethyl;

Z is —N= or —CH=;

X is oxygen or sulfur;

R$_1'$ is halo, trifluormethyl, nitro, cyano, C$_1$-C$_4$-alkyl or C$_1$-C$_4$-alkoxy; and n represents 0, 1, 2 or 3.

which comprises applying to the crops, their environs, or the seeds from which the crops are grown, a herbicidally-antagonistic active amount of a 1,5-diphenyl-pyrazole-3-carboxylic acid derivative of the formula

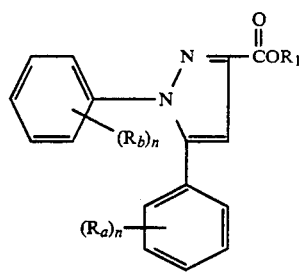

in which R$_1$ is (i) hydrogen;

(ii) a plant-physiologically acceptable metal or ammonium cation;

(iii) an unsubstituted, monosubstituted or polysubstituted alkyl group of 1 to 18 carbon atoms or cycloalkyl group of 3 to 18 carbon atoms in which the substituents are selected from the group consisting of alkenyl of 2 to 8 carbon atoms, alkynyl of 2 to 8 carbon atoms, cycloalkenyl of 3 to 8 carbon atoms, halo, nitro, cyano, alkoxy of 1 to 4 carbon atoms, alkoxycarbonyl of 1 to 4 carbon atoms, alkylcarbonyl of 1 to 4 carbon atoms, carbamoyl, dialkylcarbamoyl in which each alkyl group has 1 to 4 carbon atoms, amino, alkylamino of 1 to 4 carbon atoms, and dialkylamino in which each alkyl group has 1 to 4 carbon atoms;

(iv) the group -U in which U is unsubstituted, monosubstituted or polysubstituted phenyl or naphthyl in which the substituents are selected from the group consisting of of halo, alkyl of 1 to 4 carbon atoms, alkoxy of 1 to 4 carbon atoms, alkythio of 1 to 4 carbon atoms, alkylsulfinyl of 1 to 4 carbon atoms, alkylsulfonyl of 1 to 4 carbon atoms, haloalkyl of 1 to 4 carbon atoms, haloalkoxy of 1 to 4 carbon atoms, cyano, nitro, carboxy, alkoxycarbonyl of 1 to 4 carbon atoms, alkylcarbonyl of 1 to 4 carbon atoms, carbamoyl, alkylcarbamoyl of 1 to 4 carbon atoms, dialkylcarbamoyl wherein each alkyl group has 1 to 4 carbon atoms, sulfamoyl, alkylsulfamoyl of 1 to 4 carbon atoms, dialkylsulfamoyl wherein each alkyl group has 1 to 4 carbon atoms, pyrrolidino, piperidino, pyrrolidinocarbonyl, piperidcinocarbonyl, and morpholinocarbonyl; or (v) the group -EU in which U is as herein defined and E is alkylene of 1 to 4 carbon atoms, alkenylene of 2 to 4 carbon atoms, or alkynylene of 2 to 4 carbon atoms;

R$_a$ is hydrogen, halo, alkyl of 1 to 5 carbon atoms, haloalkyl of 1 to 5 carbon atoms, alkenyl of 2 to 5 carbon atoms, alkynyl of 2 to 5 carbon atoms, or cyano; R$_b$ is halo, alkyl of 1 to 5 carbon atoms, haloalkyl of 1 to 5 carbon atoms, alkenyl of 2 to 5 carbon atoms, alkynyl of 2 to 5 carbon atoms, or cyano; and each n, independently of the other, has a value of 0 to 3 with the proviso that when Ra is hydrogen, R$_1$ is hydrogen or ethyl, and R6 is methyl or halo, R6 is in the ortho position.

2. A method for the selective control of weeds in crops of useful plants, characterised in that the crops or the areas in which they are grown are treated a) with a herbicidally effective amount of a herbicide of the formula

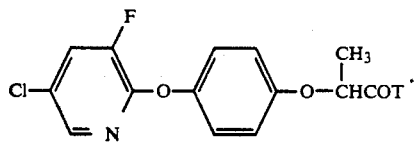

in which T is methoxy, ethoxy, propoxy, isopropoxy, butoxy, dimethylaminoethoxy, propargyloxy, 1-cyano-1-methylethoxy, methylcarbonylmethylthio, 1-ethoxycarbonylethoxy, butoxycarbony, acetoximoxy, methylethylketoximoxy, or cyclohexanoximoxy, and b) either at the same or a different ime with a herbicidally-antagonistic effective amount of a 1,5-diphenylpyrazole-3-carboxylic acid derivative of the formula:

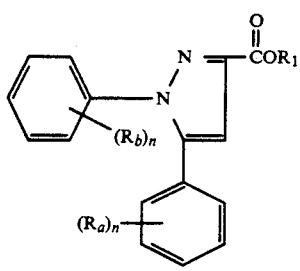

in which $R_1$ is
(i) hydrogen;
(ii) a plant-physiologically acceptable metal or ammonium cation;
(iii) an unsubstituted, monosubstituted or polysubstituted alkyl group of 1 to 18 carbon atoms or cycloalkyl group of 3 to 18 carbon atoms in which the substituents are selected from the group consisting of alkenyl of 2 to 8 carbon atoms, alkynyl of 2 to 8 carbon atoms, cycloalkenyl of 3 to 8 carbon atoms, halo, nitro, cyano, alkoxy of 1 to 4 carbon atoms, alkoxycarbonyl of 1 to 4 carbon atoms, alkylcarbonyl of 1 to 4 carbon atoms, carbamoyl, dialkylcarbamoyl in which each alkyl group has 1 to 4 carbon atoms, amino, alkylamino of 1 to 4 carbon atoms, and dialkylamino in which each alkyl group has 1 to 4 carbon atoms;
(iv) the group -U in which U is unsubstituted, monosubstituted or polysubstituted phenyl or naphthyl in which the substituents are selected from the group consisting of halo, alkyl of 1 to 4 carbon atoms, alkoxy of 1 to 4 carbon atoms, alkythio of 1 to 4 carbon atoms, alkylsulfinyl of 1 to 4 carbon atoms, alkylsulfonyl of 1 to 4 carbon atoms, haloalkyl of 1 to 4 carbon atoms, haloalkoxy of 1 to 4 carbon atoms, cyano, nitro, carboxy, alkoxycarbonyl of 1 to 4 carbon atoms, alkylcarbonyl of 1 to 4 carbon atoms, carbamoyl, alkylcarbamoyl of 1 to 4 carbon atoms, dialkylcarbamoyl wherein each alkyl group has 1 to 4 carbon atoms, sulfamoyl, alkylsulfamoyl of 1 to 4 carbon atoms, dialkylsulfamoyl wherein each alkyl group has 1 to 4 carbon atoms, pyrrolidino, piperidino, pyrrolidinocarbonyl, piperidcinocarbonyl, and morpholinocarbonyl; or
(v) the group -EU in which U is as herein defined and E is alkylene of 1 to 4 carbon atoms, alkenylene of 2 to 4 carbon atoms, or alkynylene of 2 to 4 carbon atoms;

$R_a$ is hydrogen, halo, alkyl of 1 to 5 carbon atoms, haloalkyl of 1 to 5 carbon atoms, alkenyl of 2 to 5 carbon atoms, alkynyl of 2 to 5 carbon atoms, or cyano;

$R_b$ is halo, alkyl of 1 to 5 carbon atoms, haloalkyl of 1 to 5 carbon atoms, alkenyl of 2 to 5 carbon atoms, alkynyl of 2 to 5 carbon atoms, or cyano; and each n, independently of the other, has a value of 0 to 3 with the proviso that when Ra is hydrogen, $R_1$ is hydrogen or ethyl, and R6 is methyl or halo, R6 is in the ortho position.

3. The method according to claim 2 wherein in said 1,5-diphenylpyrazole-3-carboxylic acid derivative, $R_1$ is alkyl of 1 to 18 carbon atoms, which is unsubstituted, monosubstituted or polysubstituted with alkenyl of 2 to 6 carbon atoms, alkynyl of 2 to 8 carbon atoms, halo, nitro, cyano, or alkoxy of 1 to 4 carbon atoms.

4. The method according to claim 2 wherein in said 1,5-diphenylpyrazole-3-carboxylic acid derivative, $R_1$ is a plant-physiologically acceptable metal or ammonium cation.

5. The method according to claim 2 wherein in said 1,5-diphenylpyrazole-3-carboxylic acid derivative
$R_1$ is alkyl of 1 to 18 carbon atoms, which is unsubstituted, monosubstituted or polysubstituted with alkenyl of 2 to 8 carbon atoms, alkynyl of 2 to 8 carbon atoms, halo, nitro, cyano, or alkoxy of 1 to 4 carbon atoms;
$R_a$ is hydrogen, halo, or alkoxy of 1 to 4 carbon atoms;
$R_b$ is halo, alkyl of 1 to 4 carbon atoms, alkoxy of 1 to 4 carbon atoms, or nitro; and
n is 0 or 1.

6. The method of claim 2 wherein said 1,5-diphenylpyrazole-3-carboxylic acid is 1-(2-chlorophenyl)-3-methoxycarbonyl-5-phenylpyrazole.

7. The method of claim 2 wherein said 1,5-diphenylpyrazole-3-carboxylic acid is 1-(2,4-chlorophenyl)-3-methoxycarbonyl-5-phenylpyrazole.

8. The method of claim 2 wherein said 1,5-diphenylpyrazole-3-carboxylic acid is 1-(2-chlorophenyl)-3-methoxycarbonyl-5-(2-fluorophenyl)pyrazole.

9. The method according to claim 2 wherein said herbicide is propargyl 2-[4-(3-fluoro-5-chloropyridin-2-yloxy) phenoxy]propionate.

10. The method according to claim 2 wherein said herbicide is methyl 2-[4-(3-fluoro-5-chloropyridin-2yloxy) phenoxy]propionate.

* * * * *